United States Patent
Drago et al.

(10) Patent No.: US 9,243,292 B2
(45) Date of Patent: Jan. 26, 2016

(54) METHOD FOR THE GENOMIC TYPING OF ERYTHROCYTE SYSTEMS, OLIGONUCLEOTIDE PROBES AND RELATIVE DIAGNOSTIC KITS

(75) Inventors: Francesca Drago, Milan (IT); Katerina Karpasitou, Milan (IT); Francesca Poli, Monza (IT)

(73) Assignee: FONDAZIONE IRCCS CA' GRANDA-OSPEDALE MAGGIORE POLICLINICO, Milan (IT)

( * ) Notice: Subject to any disclaimer, the term of this patent is extended or adjusted under 35 U.S.C. 154(b) by 827 days.

(21) Appl. No.: 12/450,172

(22) PCT Filed: Mar. 11, 2008

(86) PCT No.: PCT/EP2008/002012
§ 371 (c)(1),
(2), (4) Date: Sep. 21, 2009

(87) PCT Pub. No.: WO2008/110367
PCT Pub. Date: Sep. 18, 2008

(65) Prior Publication Data
US 2010/0143904 A1     Jun. 10, 2010

(30) Foreign Application Priority Data

Mar. 13, 2007  (IT) .............................. MI2007A0504

(51) Int. Cl.
*C12P 19/34*  (2006.01)
*C12Q 1/68*  (2006.01)

(52) U.S. Cl.
CPC ............ *C12Q 1/6881* (2013.01); *C12Q 1/6837* (2013.01); *C12Q 2600/156* (2013.01); *C12Q 2600/16* (2013.01)

(58) Field of Classification Search
CPC .. C12Q 1/6881; C12Q 1/6837; C12Q 1/6888; C12Q 1/6844

USPC ................................................. 435/6.1, 91.2
See application file for complete search history.

(56) References Cited

FOREIGN PATENT DOCUMENTS

| WO | WO 9615268 | * | 5/1996 |
|---|---|---|---|
| WO | WO2005/095650 A | | 10/2005 |
| WO | WO2006/047471 A | | 5/2006 |
| WO | WO2006/075254 A | | 7/2006 |
| WO | WO2006/079925 A | | 8/2006 |

OTHER PUBLICATIONS

PCT Search Report dated Sep. 4, 2008.
Drago, F. et al.; Genotyping of the Kidd blood group with allele-specific nucleotides coupled to fluorescent microspheres;Transfusion Medicine, Oxford, GB;vol. 15, No. 6; pp. 499-501; Dec. 2005.
Hashimi Ghazala et al.; A flexible array format for large-scale, rapid blood group DNA typing; Transfusion(Malden); vol. 45, No. 5; pp. 680-688; (May 2005).
Beiboer S.H.W. et al.; Rapid genotyping of blood group antigens by multiplex polymrerase chainreaction and DNA microarray hybridization; Transfusion Amer. Assoc. of Blood Banks, Bethesda, MD; vol. 45, No. 5; pp. 667-679; May 2005.
Denomme G.A. et al.; High-throughput multiplex single-nucleotide polymorphism analysis for red cell and platelet antigen genotypes; Transfusion Amer. Assoc. of Blood Banks, Bethesda, MD; vol. 45, No. 5; pp. 660-666; May 2005.
Karpasitou Katerina et al.; Blood group genotyping for Jk(a)/Jk(b), Fy(a)/Fy(b),S/s, K/k,Kp(a)/Kp(b), Js(a)/Js(b),Co(a)/Co/(b), and Lu(a)/Ku(b) with microarray beads; Transfusion; vol. 48, No. 3; pp. 505-512; Feb. 2008.

* cited by examiner

*Primary Examiner* — Cynthia B Wilder
(74) *Attorney, Agent, or Firm* — Hedman & Costigan, P.C.; James V. Costigan; Kathleen A. Costigan

(57) ABSTRACT

The invention relates to a method for the genomic typing of erythrocyte systems, oligonucleotide probes and relative diagnostic kits.

5 Claims, 1 Drawing Sheet

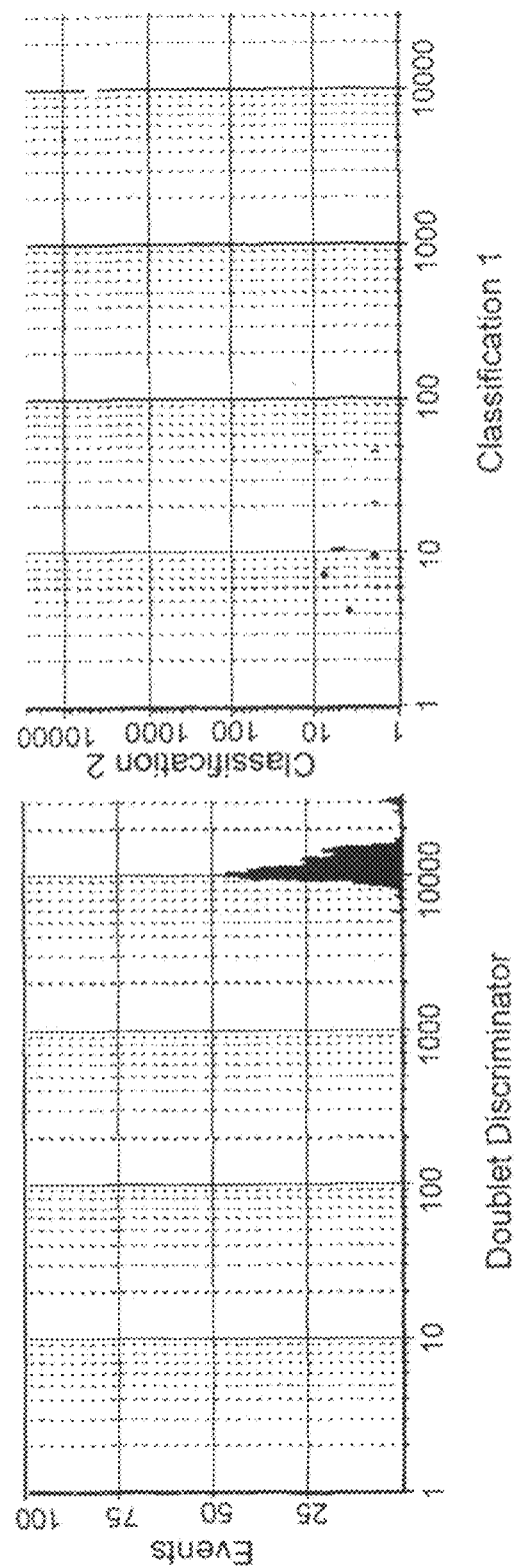

SEQUENCE LISTING

```
<160> NUMBER OF SEQ ID NOS: 40

<210> SEQ ID NO 1
<211> LENGTH: 24
<212> TYPE: DNA
<213> ORGANISM: Artificial
<220> FEATURE:
<223> OTHER INFORMATION: K5F Forward primer

<400> SEQUENCE: 1
tttagtcctc actcccatgc ttcc                                          24

<210> SEQ ID NO 2
<211> LENGTH: 24
<212> TYPE: DNA
<213> ORGANISM: Artificial
<220> FEATURE:
<223> OTHER INFORMATION: K6R Forward primer

<400> SEQUENCE: 2
tatcacacag gtgtcctctc ttcc                                          24

<210> SEQ ID NO 3
<211> LENGTH: 19
<212> TYPE: DNA
<213> ORGANISM: Artificial
<220> FEATURE:
<223> OTHER INFORMATION: KpF forward primer

<400> SEQUENCE: 3
tgaggccagg agaaaagca                                                19

<210> SEQ ID NO 4
<211> LENGTH: 21
<212> TYPE: DNA
<213> ORGANISM: Artificial
<220> FEATURE:
<223> OTHER INFORMATION: KpR Reverse primer

<400> SEQUENCE: 4
tgaccatctg gaagagcttg c                                             21

<210> SEQ ID NO 5
<211> LENGTH: 19
<212> TYPE: DNA
<213> ORGANISM: Artificial
<220> FEATURE:
<223> OTHER INFORMATION: JsF Forward primer

<400> SEQUENCE: 5
aactttgcca tgctcctgg                                                19

<210> SEQ ID NO 6
<211> LENGTH: 20
<212> TYPE: DNA
<213> ORGANISM: Artificial
<220> FEATURE:
<223> OTHER INFORMATION: JsR Reverse primer
```

```
<400> SEQUENCE: 6
gccttgacac ttgcatacct                                              20

<210> SEQ ID NO 7
<211> LENGTH: 23
<212> TYPE: DNA
<213> ORGANISM: Artificial
<220> FEATURE:
<223> OTHER INFORMATION: Lu91mF Forward primer

<400> SEQUENCE: 7
ctgaggagcg ctgggacacc cgg                                          23

<210> SEQ ID NO 8
<211> LENGTH: 18
<212> TYPE: DNA
<213> ORGANISM: Artificial
<220> FEATURE:
<223> OTHER INFORMATION: Lu92R Reverse primer

<400> SEQUENCE: 8
ccccgggtgt cgtgcatt                                                18

<210> SEQ ID NO 9
<211> LENGTH: 20
<212> TYPE: DNA
<213> ORGANISM: Artificial
<220> FEATURE:
<223> OTHER INFORMATION: SsF Forward primer

<400> SEQUENCE: 9
aagactgaca cattacctca                                              20

<210> SEQ ID NO 10
<211> LENGTH: 20
<212> TYPE: DNA
<213> ORGANISM: Artificial
<220> FEATURE:
<223> OTHER INFORMATION: SsR Reverse primer

<400> SEQUENCE: 10
aacatacctg gtacagtgaa                                              20

<210> SEQ ID NO 11
<211> LENGTH: 20
<212> TYPE: DNA
<213> ORGANISM: Artificial
<220> FEATURE:
<223> OTHER INFORMATION: CoF3 Forward primer

<400> SEQUENCE: 11
tataaatagg cccagcccag                                              20

<210> SEQ ID NO 12
<211> LENGTH: 19
<212> TYPE: DNA
<213> ORGANISM: Artificial
<220> FEATURE:
<223> OTHER INFORMATION: CoR3 Reverse primer

<400> SEQUENCE: 12
ccagcgacac cttcacgtt                                               19

<210> SEQ ID NO 13
```

```
<211> LENGTH: 21
<212> TYPE: DNA
<213> ORGANISM: Artificial
<220> FEATURE:
<223> OTHER INFORMATION: Duffy-F2 Forward primer

<400> SEQUENCE: 13
cttccggtgt aactctgatg g                                              21

<210> SEQ ID NO 14
<211> LENGTH: 21
<212> TYPE: DNA
<213> ORGANISM: Artificial
<220> FEATURE:
<223> OTHER INFORMATION: Duffy R3 Reverse primer

<400> SEQUENCE: 14
catccagcag gttacaggag t                                              21

<210> SEQ ID NO 15
<211> LENGTH: 22
<212> TYPE: DNA
<213> ORGANISM: Artificial
<220> FEATURE:
<223> OTHER INFORMATION: JK-78-F3 Forward primer

<400> SEQUENCE: 15
catgctgcca taggatcatt gc                                             22

<210> SEQ ID NO 16
<211> LENGTH: 20
<212> TYPE: DNA
<213> ORGANISM: Artificial
<220> FEATURE:
<223> OTHER INFORMATION: JK-943-R3 Reverse primer

<400> SEQUENCE: 16
gagccaggag gtgggtttgc                                                20

<210> SEQ ID NO 17
<211> LENGTH: 18
<212> TYPE: DNA
<213> ORGANISM: Artificial
<220> FEATURE:
<223> OTHER INFORMATION: k probe sequence

<400> SEQUENCE: 17
ttaaccgaac gctgagac                                                  18

<210> SEQ ID NO 18
<211> LENGTH: 18
<212> TYPE: DNA
<213> ORGANISM: Artificial
<220> FEATURE:
<223> OTHER INFORMATION: K probe sequence

<400> SEQUENCE: 18
ttaaccgaat gctgagac                                                  18

<210> SEQ ID NO 19
<211> LENGTH: 18
<212> TYPE: DNA
<213> ORGANISM: Artificial
<220> FEATURE:
<223> OTHER INFORMATION: Negative control probe

<400> SEQUENCE: 19
```

```
ctatcccaaa gctaaggc                                                    18

<210> SEQ ID NO 20
<211> LENGTH: 20
<212> TYPE: DNA
<213> ORGANISM: Artificial
<220> FEATURE:
<223> OTHER INFORMATION: Kpb probe sequence

<400> SEQUENCE: 20
atcacttcac ggctgttcca                                                  20

<210> SEQ ID NO 21
<211> LENGTH: 20
<212> TYPE: DNA
<213> ORGANISM: Artificial
<220> FEATURE:
<223> OTHER INFORMATION: Kpa probe sequence

<400> SEQUENCE: 21
tcacttcatg gctgttccag                                                  20

<210> SEQ ID NO 22
<211> LENGTH: 20
<212> TYPE: DNA
<213> ORGANISM: Artificial
<220> FEATURE:
<223> OTHER INFORMATION: Negative control probe

<400> SEQUENCE: 22
aactctacgg ggctcttcga                                                  20

<210> SEQ ID NO 23
<211> LENGTH: 20
<212> TYPE: DNA
<213> ORGANISM: Artificial
<220> FEATURE:
<223> OTHER INFORMATION: Jsb probe sequence

<400> SEQUENCE: 23
ggctgcctcg cctgtgacaa                                                  20

<210> SEQ ID NO 24
<211> LENGTH: 20
<212> TYPE: DNA
<213> ORGANISM: Artificial
<220> FEATURE:
<223> OTHER INFORMATION: Jsa probe sequence

<400> SEQUENCE: 24
ggctgccccg cctgtgacaa                                                  20

<210> SEQ ID NO 25
<211> LENGTH: 20
<212> TYPE: DNA
<213> ORGANISM: Artificial
<220> FEATURE:
<223> OTHER INFORMATION: Negative control probe

<400> SEQUENCE: 25
gccagccacg cgtgtcacta                                                  20

<210> SEQ ID NO 26
<211> LENGTH: 18
<212> TYPE: DNA
```

```
<213> ORGANISM: Artificial
<220> FEATURE:
<223> OTHER INFORMATION: Lua probe sequence

<400> SEQUENCE: 26 tcgccccgc ctagcctc                                                    18

<210> SEQ ID NO 27
<211> LENGTH: 18
<212> TYPE: DNA
<213> ORGANISM: Artificial
<220> FEATURE:
<223> OTHER INFORMATION: Lub probe sequence

<400> SEQUENCE: 27 tcgccccac ctagcctc                                                    18

<210> SEQ ID NO 28
<211> LENGTH: 18
<212> TYPE: DNA
<213> ORGANISM: Artificial
<220> FEATURE:
<223> OTHER INFORMATION: Negative control probe

<400> SEQUENCE: 28
tagcctcctc caagacta                                                   18

<210> SEQ ID NO 29
<211> LENGTH: 20
<212> TYPE: DNA
<213> ORGANISM: Artificial
<220> FEATURE:
<223> OTHER INFORMATION: s probe sequence

<400> SEQUENCE: 29
taggagaaac gggacaactt                                                 20

<210> SEQ ID NO 30
<211> LENGTH: 20
<212> TYPE: DNA
<213> ORGANISM: Artificial
<220> FEATURE:
<223> OTHER INFORMATION: S probe sequence

<400> SEQUENCE: 30
aggagaaatg ggacaacttg                                                 20

<210> SEQ ID NO 31
<211> LENGTH: 20
<212> TYPE: DNA
<213> ORGANISM: Artificial
<220> FEATURE:
<223> OTHER INFORMATION: Negative control probe

<400> SEQUENCE: 31
tcggataaaa gagaccactg                                                 20

<210> SEQ ID NO 32
<211> LENGTH: 20
<212> TYPE: DNA
<213> ORGANISM: Artificial
<220> FEATURE:
<223> OTHER INFORMATION: Coa probe sequence

<400> SEQUENCE: 32
aaccagacgg cggtccagga                                                 20
```

<210> SEQ ID NO 33
<211> LENGTH: 20
<212> TYPE: DNA
<213> ORGANISM: Artificial
<220> FEATURE:
<223> OTHER INFORMATION: Cob probe sequence

<400> SEQUENCE: 33
caaccagacg gtggtccagg                                              20

<210> SEQ ID NO 34
<211> LENGTH: 20
<212> TYPE: DNA
<213> ORGANISM: Artificial
<220> FEATURE:
<223> OTHER INFORMATION: Negative control probe

<400> SEQUENCE: 34
agccacactg gggacctgga                                              20

<210> SEQ ID NO 35
<211> LENGTH: 20
<212> TYPE: DNA
<213> ORGANISM: Artificial
<220> FEATURE:
<223> OTHER INFORMATION: Fya probe sequence

<400> SEQUENCE: 35
gagactatgg tgccaacctg                                              20

<210> SEQ ID NO 36
<211> LENGTH: 20
<212> TYPE: DNA
<213> ORGANISM: Artificial
<220> FEATURE:
<223> OTHER INFORMATION: Fyb probe sequence

<400> SEQUENCE: 36
tggagactat gatgccaacc                                              20

<210> SEQ ID NO 37
<211> LENGTH: 20
<212> TYPE: DNA
<213> ORGANISM: Artificial
<220> FEATURE:
<223> OTHER INFORMATION: Negative control probe

<400> SEQUENCE: 37
gaggctatcc tgacaagctt                                              20

<210> SEQ ID NO 38
<211> LENGTH: 18
<212> TYPE: DNA
<213> ORGANISM: Artificial
<220> FEATURE:
<223> OTHER INFORMATION: Jka probe sequence

<400> SEQUENCE: 38
agtagatgtc ctcaaatg                                                18

<210> SEQ ID NO 39
<211> LENGTH: 21
<212> TYPE: DNA
<213> ORGANISM: Artificial
<220> FEATURE:

```
<223> OTHER INFORMATION: Jkb probe sequence

<400> SEQUENCE: 39
aggtaggatg gttctcaaat g                                          21

<210> SEQ ID NO 40
<211> LENGTH: 18
<212> TYPE: DNA
<213> ORGANISM: Artificial
<220> FEATURE:
<223> OTHER INFORMATION: Negative control probe

<400> SEQUENCE: 40
cgtggatttc ttcagagg                                              18
```

METHOD FOR THE GENOMIC TYPING OF ERYTHROCYTE SYSTEMS, OLIGONUCLEOTIDE PROBES AND RELATIVE DIAGNOSTIC KITS

The present invention relates to a method for the genomic typing of erythrocyte systems, oligonucleotide probes and relative diagnostic kits.

Blood group typing has been traditionally performed with agglutination techniques using various methods such as slides, tubes, columns and solid/liquid phase microplate technology with both polyclonal and monoclonal commercial antisera.

The various agglutination techniques which can be applied in all competent laboratories have a sensitivity and appropriate specificity in clinical use for most cases.

However, due to limitations in hemagglutination, it is now customary in reference laboratories, to complement and support serologic blood group typing with molecular techniques and in many cases are the sole alternative method capable of solving complex problems.

There are various applications in transfusion medicine practice.

Most clinical applications appropriately respond to the demand for having a correct blood group typing of the patient in a short time and relate to multi-immunized subjects with autoimmune pathologies, to patients transfused immediately prior to blood group testing and/or transfusion-dependent patients such as thalassemic patients (ref. 1 Castilho L. et al. 2002; ref. 2 Montalvo L. et al. 2004). In these cases, typing with classical methods could be difficult to apply. For the first category of patients, difficulties arise due to the presence of antibodies adhering to the erythrocytes which require additional analyses and different typing methods on the part of the laboratory for immunohematological analyses, considerably prolonging the analysis time which is precious in emergency situations. In the second category of patients transfused immediately prior to blood group testing, the problem is due to the presence of massive quantities of transfused erythrocytes of the donor in the patient's circulation rendering it impossible to apply classical methods. In this case therefore, a correct typing of the patient's RH phenotype and of other common red blood cell antigens (for example, K/k; Fya/Fyb; Jka/Jkb; S/s) against which the development of antibodies may have a relevant clinical meaning, is extremely useful for confirming the nature of the antibodies identified both in the serum and adhering to the erythrocytes and consequently for providing the best possible transfusion support for the patient.

There are other interesting applications of the molecular typing of erythrocyte systems. These include the confirmation and at times the only resolution source in cases of antigens with weak expression such as the D antigen (RH system) or FyX antigen (Duffy system); the characterization of null forms; the determination of D-zygosity not otherwise possible and resolution in cases of ABO variants.

Another important application also relates to the possibility of confirming, with molecular techniques, the rare erythrocyte typing of patients or blood donors who are negative for high incidence antigens. A person having a rare phenotype can become immunized against the missing antigen following transfusion, pregnancy and to a lesser extent organ transplant. Immunization against a high incidence antigen can also complicate considerably the detection of additional blood group antibodies. The presence of antibodies having different specificities makes the identification process laborious and complicated and the finding of compatible blood units extremely problematical.

The possibility of having frozen typed blood units at the moment of need considerably facilitates patient management, without having to resort to the random typing of a high number of donors under emergency conditions, also with the risk of not finding the compatible unit. Rare blood units could be frozen and isolated for patients at risk. Furthermore, it should also be taken into consideration that ethnic differences between donor and patient could create greater problems, especially if the patient requires a long-term transfusion regime.

For this purpose, the use of molecular techniques will solve the problem of the high costs of rare antisera and at times, for some specificities, it also overcomes the problem of both the lack of and weak reactivity of these easily perishable antisera such as the specific antisera for the Dombrock system (ref. 3 Reid et al. 2002).

An important advantage of DNA methods consists in the possibility of obtaining a useful DNA quantity from both peripheral blood, even from minimum quantities, and other biological sources. Furthermore, if the DNA samples are appropriately preserved, they are stable over a long period of time. Working with DNA in transfusion medicine has also the considerable advantage of not being limited by the fact that the sample must be processed immediately as required by classical serology.

Various techniques applied in the field of transfusion medicine have been developed for all these potential applications. In particular, for blood group genotyping, the most common techniques used in immunohematology laboratories are PCR-RFLP (Restriction Fragment Length Polymorphism) and PCR-SSP (Sequence-Specific Primers).

New methods have been recently developed such as PCR-ELISA, real time PCR, SNP minisequencing analyses (ref. 4 Ferri E G et al., 2006) and microarray technology (ref. 5 Denomme G. et al., 2005). This latter technology in particular arose from the necessity to type a greater number of samples with respect to other available techniques which were low-throughput.

The principle of this technique is certainly not entirely new. The Southern blot techniques, for example, provides for the analysis of a large number of samples by hybridization of DNA fragments but by means of electrophoresis. The main difference lies in the type of material used as hybridization support; porous hybridization membranes have been replaced with non-porous glass or silicon support or fluorescently-labeled microspheres (ref. 6 Petrik J. 2001). These changes have allowed reagent volumes to be considerably reduced, improving the hybridization kinetics, miniaturizing the whole process, increasing throughput and allowing the possibility to test for several analytes contemporaneously in a single reaction. All these revolutionary changes reduce considerably operator-time, laboriousness and costs.

A variety of applications of the microarray technology have been developed in recent years. This technology is applied in both genetic analysis and serology.

The microarray technology, as applied in this case, is characterized by an amplification phase of the target DNA region, followed by denaturation, hybridization with specific probes complementary to the target polymorphism and fluorescence detection and data analysis by means of flow cytometry after suitable marking with phycoerythrin-streptavidin. With microarray technology using a solid hybridization support, it is possible to type antigens from the ABO and RH systems as well as clinically significant and high incidence antigens. This technology has also been applied to the genomic typing of platelet antigens (ref. 7 Beiboer S. et al., 2005). Furthermore, the use of agglutination techniques involves high costs in the case of mass screening for high incidence erythrocyte antigens in order to obtain negative donors, as the availability of commercial typing reagents is extremely limited, also making typing with antisera problematic due to poor reliability.

One of the main advantages of techniques based on DNA is the substitution of typing sera by oligonucleotides synthesized at low cost.

The new technologies currently seem to aim at automation and simplification and the new instruments are modified to accelerate the process. This latter concept is descriptive of dosages of multiplex flow cytometry based on microspheres. By the coupling of various purified antibodies or oligonucleotide probes to distinct sets of fluorescent microspheres, it is possible to obtain extremely efficient analysis systems which allow numerous analytes to be captured from a single sample. The quantification exploits the multiparametric resolutive potential of flow cytometry and the capacity of the processing systems of the digital signals which process the thousands of fluorescent signals generated by the microspheres (ref. 8 Kellar K L et al., 2003; ref. 9 Kettman J R et al., 1998).

More specifically, the microspheres consist of synthetic polymers and each microsphere set is characterized by a specific fluorescence intensity. Various commercial sources of fluorescent microspheres are available such as Bangs Laboratories (Fishers, Ind.), Duke Scientific (Palo Alto, Calif.), Luminex Corporation (Austin, Tex.), Polysciences (Warrington, Pa.), Seradyn (Indianapolis, Ind.) and Sperotech (Libertyville, Ill.) which offer microspheres with different dimensions and fluorescence characteristics. Luminex Corporation, for example, produces 100 microspheres differing in fluorescence intensity created by the incorporation of different ratios of two fluorochromes which emit at different wavelengths (ref. 10 Fulton R F et al., 1997). A compact flow cytometer (Luminex 100) with two projected laser sources is used for the detection of the microspheres and quantification of the fluorescence. An array of 100 microspheres has been produced with dyes which emit at 658 and 712 nm after stimulation with a 635 nm red diode laser to complement the laser system of the cytometer (ref. 11 Earley M C et al. 2002). This Multiple Analyte Profiling system (LabMAP™) was used for the multiplex analysis of various single nucleotide polymorphisms (SNPs) (ref. 12 Colinas et al., 2000; ref. 13 Dunbar S A et al., 2000). SNPs are the most abundant variability source in the human genome, important for the identification of particular pathologies or for clarifying the predisposition for developing a particular illness or responding to a certain pharmacological therapy (ref. 8 Kellar K L, 2003). SNPs also represent the molecular basis of the polymorphisms of numerous antigen systems.

The authors have now set up a molecular blood group typing method which uses specific oligonucleotide probes which, when suitably modified, are coupled to an array of fluorescent microspheres, which does not have the disadvantages of the known typing techniques.

By using the method according to the invention, there is a considerable reduction in reagent costs and operator time.

From an applicative point of view, the method is particularly advantageous for the large-scale typing of blood samples and can facilitate the identification of a rare phenotype for alloimmunized patients and subjects belonging to ethnic minorities. More specifically, in the present invention, after identifying the polymorphism Xa and Xb relating to each of the systems subject of the study, the authors designed oligonucleotide probes capable of hybridizing, at a certain temperature, in a highly specific manner, at the polymorphic site of interest. These probes have given excellent results in terms of specificity and efficiency of the hybridization process (selected probe length/polymorphism/hybridization temperature).

The characteristics and advantages of the method and the experimental phases set up by the authors of the present invention and used in the present typing method are the following:

application of the Luminex suspension array method to the genotyping of blood group systems.

identification of pairs of specific primers for amplifying the genomic region containing the single nucleotide polymorphism of interest (see Table 1).

identification of PCR conditions: same quantity and concentration ratios for both the primers and buffers used and same amplification cycles for all the systems studied.

design of the oligonucleotide probes: designed complementary to the sequence amplified by the biotinylated primer, with localization of the polymorphism of interest at or near the centre of the probe (the polymorphic position is marked in bold in Table 2). The changes with respect to the central position are determined by the addition and/or removal of nucleotides from the 5'- and/or 3'-end of the probe to increase the hybridization efficiency and obtain a better probe-target match or to increase the specificity (ref. 14 Dunbar S A et al., 2005; ref. 15 Dunbar S A. Et al., 2006).

direct hybridization of the designed probes with the PCR product, containing the polymorphism object of the study, at a specific hybridization temperature range defined for each system studied, wherein the optimal specific hybridization temperature is shown in parenthesis (see Table 2).

TABLE 1

| System | Target alleles | Name of primer | Sequence (5'-3') |
|---|---|---|---|
| KELL | K/k PCR1 | K5F ref. 16 K6R ref. 16 | TTTAgTCCTCACTCCCATgCTTCC (SEQ ID NO: 1) TATCACACAggTgTCCTCTCTTCC (SEQ ID NO: 2) |
|  | Kpa/Kpb PCR2 | KpF KpR | TgAggCCAggAgAAAAgCA (SEQ ID NO: 3) TgACCATCTggAAgAgCTTgC (SEQ ID NO: 4) |
|  | Jsa/Jsb PCR2 | JsF JsR | AACTTTgCCATgCTCCTgg (SEQ ID NO: 5) GCCTTgACACTTgCATACCT (SEQ ID NO: 6) |
| LUTHERAN | Lua/Lub PCR3 | Lu91mF Lu92R ref. 18 | CTgAggAgCgCTgggACACCCgg (SEQ ID NO: 7) CCCCgggTgTCgTgCATT (SEQ ID NO: 8) |

TABLE 1-continued

| System | Target alleles | Name of primer | Sequence (5'-3') |
|---|---|---|---|
| MNS | S/s PCR4 | SsF ref. 17 | AAgACTgACACATTACCTCA (SEQ ID NO: 9) |
|  |  | SsR | AACATACCTggTACAgTgAA (SEQ ID NO: 10) |
| COLTON | Coa/Cob PCR5 | CoF3 | TATAAATAggCCCAgCCCAg (SEQ ID NO: 11) |
|  |  | CoR3 | CCAgCgACACCTTCACgTT (SEQ ID NO: 12) |
| DUFFY | Fya/Fyb PCR6 | Duffy-F2 | CTTCCggTgTAACTCTgATgg (SEQ ID NO: 13) |
|  |  | Duffy-R3 | CATCCAgCAggTTACAggAgT (SEQ ID NO: 14) |
| KIDD | Jka/Jkb PCR7 | JK-781 F3 ref. 19 | CATgCTgCCATAggATCATTgC (SEQ ID NO: 15) |
|  |  | JK-943 R3 ref. 19 | gAgCCAggAggTgggTTTgC (SEQ ID NO: 16) | ref. 16 Lee, 1997
ref. 17 Hashmi, 2005
ref. 18 El Nemer, 1997
ref. 19 Irshaid, 1998.

TABLE 2

| Target alleles | Probe AmC12-5' | $T_{HYB}$ RANGE | Microspheres Specificity/ Region N. |
|---|---|---|---|
| K/k | TTAACCgAACgCTgAgAC (SEQ ID NO 17) | 45-50° C. | K-088 |
|  | TTAACCgAATgCTgAgAC (SEQ ID NO 18) | (45° C. | k-089 |
|  | CTATCCCAAAgCTAAggC (SEQ ID NO 19) |  | NC-086 |
| Kpa/ Kpb | ATCACTTCACggCTGTTCCA (SEQ ID NO 20) | 52-56° C. | Kpa-072 |
|  | TCACTTCATggCTgTTCCAg (SEQ ID NO 21) | (54° C. | Kpb-073 |
|  | AACTCTACAgggCTCTTCgA (SEQ ID NO 22) |  | NC-051 |
| Jsa/ Jsb | GgCTgCCTCgCCTgTgACAA (SEQ ID NO 23) | 52-56° C. | Jsa-053 |
|  | GgCTgCCCCgCCTgTgACAA (SEQ ID NO 24) | (54° C. | Jsb-055 |
|  | GCCAgCCACgCgTgTCACTA (SEQ ID NO 25) |  | NC-064 |
| Lua/ Lub | TCgCCCCCgCCTAgCCTC (SEQ ID NO 26) | 43-47° C. | Lua-063 |
|  | TCgCCCCCACCTAgCCTC (SEQ ID NO 27) | (45° C. | Lub-065 |
|  | TAgCCTCCTCCAAgACTA (SEQ ID NO 28) |  | NC-064 |
| S/s | TAggAgAAACgggACAACTT (SEQ ID NO 29) | 50-54° C. | S-084 |
|  | AggAgAAATgggACAACTTg (SEQ ID NO 30) | (54° C. | s-085 |
|  | TCggATAAAAgAgACCACTg (SEQ ID NO 31) |  | NC-087 |
| Coa/ Cob | AACCAgACggCggTCCAggA (SEQ ID NO 32) | 62-66° C. | Coa-074 |
|  | CAACCAgACggTggTCCAgg (SEQ ID NO 33) | (64° C. | Cob-078 |
|  | AgCCACACTggggACCTggA (SEQ ID NO 34) |  | NC-080 |
| Fya/ Fyb | GAgACTATggTgCCAACCTg (SEQ ID NO 35) | 52-56° C. | Fya-066 |
|  | TggAgACTATgATgCCAACC (SEQ ID NO 36) | (54° C. | Fyb-067 |
|  | GAggCTATCCTgACAAgCTT (SEQ ID NO 37) |  | NC-069 |
| Jka/Jkb | AgTAgATgTCCTCAAATg (SEQ ID NO 38) | 37°-40° C. | Jka-064 |
|  | AgTAgATgTTCTCAAATg (SEQ ID NO 39) | (37° C. | Jkb-076 |
|  | CgTggATTTCTTCAgAgg (SEQ ID NO 40) |  | NC-073 |

The erythrocyte systems and the relative alleles encoding common, rare and high incidence antigens, analyzed by the authors of the present invention are indicated in Table 1.

The authors then applied the Luminex Xmap technology using an array of microspheres in suspension for determining the polymorphisms relating to erythrocyte antigens in order to apply, in this field of research, the potentialities of a versatile method which provides a rapid, accurate and efficient instrument especially for the management of mass-screening. This method avails of the hybridization process between synthetic oligonucleotide capture probes coupled to fluorescent microspheres and the target DNA amplified by PCR, using specific primers which allow the genomic locus containing the nucleotide polymorphism of interest to be amplified.

The method according to the present invention was set up and tested with DNA samples of known genotype and/or phenotype (homozygote or heterozygote for the erythrocyte antigens of interest); the typing for the low incidence antigens (such as Kpa, Jsa, Lua and Cob) carried out with serologic agglutination techniques and/or molecular techniques, such as PCR-SSP, was not known for all the samples tested. The method is robust in its capacity of identifying with accuracy, on a genomic level, the polymorphism for the erythrocyte systems tested and is tolerant with respect to the quantity, quality and source of the material to be typed. Tables 3-10 indicate the values of the allelic ratios for each system studied of all the samples tested.

After DNA extraction, it is not necessary to determine DNA concentration on the spectrophotometer, thus considerably reducing operator time.

Unlike other microarray methods applied to the typing of erythrocyte or platelet systems, the specific hybridization process takes place in suspension.

From a study of recent literature, it has emerged that the specific method in question is applied in various research fields such as genotyping in the field of microbiology and virology (ref. 20 Deregt D. et al. 2006; ref. 21 Schmitt et al., 2006; ref. 22 Diaz M. et al., 2005). With respect to the microarray format using a solid support, the advantage of the array technology in suspension relates to the rapidity of data acquisition, good sensitivity and specificity and the possibility of multiplexing.

An object of the present invention therefore relates to sets of oligonucleotide probes amino-modified at the 5-end, characterized in that they have a sequence length ranging from 18 to 20 nucleotides and containing the specific SNP for each of the target alleles belonging to the genomic locus X, selected from K/k, Kpa/Kpb, Jsa/Jsb, Lua/Lub, S/s, Coa/Cob, Fya/Fyb and Jka/Jkb at or near the centre of said probe, capable of specifically hybridizing to each of said alleles; said probes being characterized in that they are coupled to a microparticle labeled with at least one fluorescent substance and that they comprise or consist of at least one set of oligonucleotide sequences indicated in the following table:

| Probe | Probe set | Probe set number |
|---|---|---|
| k | TTAACCgAACgCTgAgAC (SEQ ID NO: 17) | 1 |
| K | TTAACCgAATgCTgAgAC (SEQ ID NO: 18) | |
| NC | CTATCCCAAAgCTAAggC (SEQ ID NO: 19) | |
| Kpb | ATCACTTCACggCTgTTCCA (SEQ ID NO: 20) | 2 |
| Kpa | TCACTTCATggCTgTTCCAg (SEQ ID NO: 21) | |
| NC | AACTCTACAgggCTCTTCgA (SEQ ID NO: 22) | |
| Jsb | ggCTgCCTCgCCTgTgACAA (SEQ ID NO: 23) | 3 |
| Jsa | ggCTgCCCCgCCTgTgACAA (SEQ ID NO: 24) | |
| NC | gCCAgCCACgCgTgTCACTA (SEQ ID NO: 25) | |
| Lua | TCgCCCCCgCCTAgCCTC (SEQ ID NO: 26) | 4 |
| Lub | TCgCCCCCACCTAgCCTC (SEQ ID NO: 27) | |
| NC | TAgCCTCCTCCAAgACTA (SEQ ID NO: 28) | |
| s | TAggAgAAACgggACAACTT (SEQ ID NO: 29) | 5 |
| S | AggAgAAATgggACAACTTg (SEQ ID NO: 30) | |
| NC | TCggATAAAAgAgACCACTg (SEQ ID NO: 31) | |
| Coa | AACCAgACggCggTCCAggA (SEQ ID NO: 32) | 6 |
| Cob | CAACCAgACggTggTCCAgg (SEQ ID NO: 33) | |
| NC | AgCCACACTggggACCTggA (SEQ ID NO: 34) | |
| Fya | GAgACTATggTgCCAACCTg (SEQ ID NO: 35) | 7 |
| Fyb | TggAgACTATgATgCCAACC (SEQ ID NO: 36) | |
| NC | gAggCTATCCTgACAAgCTT (SEQ ID NO: 37) | |
| Jka | AGTAGATGTCCTCAAATG (SEQ ID NO: 38) | |

Said probes are preferably conjugated with Aminolinker C12 modification at the 5'-end.

The invention relates to the use of at least one set of oligonucleotide probes as defined in the previous table, for the identification and typing of at least one SNP of the following allelic pair X selected from K/k, Kpa/Kpb, Jsa/Jsb, Lua/Lub, S/s, Coa/Cob, Fya/Fyb, Jka/Jkb.

According to alternative embodiments of the invention, it is possible to use one or more of the oligonucleotide probe sets according to the invention in the same hybridization mixture (e.g. the sets of oligonucleotide probes for the alleles Kpa/Kpb and Jsa/Jsb or all the probe sets together).

In the present embodiment, the use of the sets of oligonucleotide probes is performed at specific hybridization temperature ranges indicated in the following Table:

| Set number | $T_{HYBRIDIZATION}$ RANGE |
|---|---|
| 1 | 45-50° C., preferably 45° C. |
| 2 | 52-56° C., preferably 54° C. |
| 3 | 52-56° C., preferably 54° C. |
| 4 | 43-47° C., preferably 45° C. |
| 5 | 50-54° C., preferably 54° C. |
| 6 | 62-66° C., preferably 64° C. |
| 7 | 52-56° C., preferably 54° C. |
| 8 | 37-40° C., preferably 37° C. |

The invention also, relates to microparticles labeled with at least one fluorescent substance having carboxylic groups on the surface, characterized in that they are coupled with at least one set of probes as defined above.

A further object of the present invention relates to a method for the identification and typing of at least one single nucleotide polymorphism (SNP) of the erythrocyte system X in heterozygote and homozygote individuals, comprising the following phases:
a) DNA extraction from a biological sample;
b) PCR amplification of the genomic locus comprising the SNP of the erythrocyte system of interest, by means of at least one specific pair of primers for a target allele selected from:

| Target alleles | Primer sequence (5'-3') |
|---|---|
| K/k | Fw: TTTAgTCCTCACTCCCATgCTTCC (SEQ ID NO: 1)<br>Rw: TATCACACAggTgTCCTCTCTTCC (SEQ ID NO: 2) |
| Kpa/Kpb | Fw: TgAggCCAggAgAAAAgCA (SEQ ID NO: 3)<br>Rw: TgACCATCTggAAgAgCTTgC (SEQ ID NO: 4) |
| Jsa/Jsb | Fw: AACTTTgCCATgCTCCTgg (SEQ ID NO: 5)<br>Rw: gCCCTTgACACTTgCATACCT (SEQ ID NO: 6) |
| Lua/Lub | Fw: CTgAggAgCgCTgggACACCCgg (SEQ ID NO: 7)<br>Rw: CCCCgggTgTCgTgCATT (SEQ ID NO: 8) |
| S/s | Fw: AAgACTgACACATTACCTCA (SEQ ID NO: 9)<br>Rw: AACATACCTggTACAgTgAA (SEQ ID NO: 10) |
| Coa/Cob | Fw: TATAAATAggCCCAgCCCAg (SEQ ID NO: 11)<br>Rw: CCAgCgACACCTTCACgTT (SEQ ID NO: 12) |
| Fya/Fyb | Fw: CTTCCggTgTAACTCTgATgg (SEQ ID NO: 13)<br>Rw: CATCCAgCAggTTACAggAgT (SEQ ID NO: 14) |
| Jka/Jkb | Fw: CATgCTgCCATAggATCATTgC (SEQ ID NO: 15)<br>Rw: gAgCCAggAggTgggTTTgC (SEQ ID NO: 16) | wherein at least one primer (Fw or Rw) is marked at the 5'-end with biotin to obtain biotinylated PCR products; the oligonucleotide probes are complementary to the DNA sequence amplified by the biotinylated primer;
c) hybridization of the biotinylated PCR products obtained in phase b) with at least one set of oligonucleotide probes as described above and labeling with streptavidin-phycoerythrin at the specific hybridization temperature range for each system as illustrated below:

| Probe | Probe set | T_HYBRIDIZATION Range |
|---|---|---|
| k | TTAACCgAACgCTgAgAC (SEQ ID NO: 17) | 45-50° C. |
| K | TTAACCgAATgCTgAgAC (SEQ ID NO: 18) | preferably 45° C. |
| NC | CTATCCCAAAgCTAAggC (SEQ ID NO: 19) | |
| Kpb | ATCACTTCACggCTgTTCCA (SEQ ID NO: 20) | 52-56° C. |
| Kpa | TCACTTCATggCTgTTCCAg (SEQ ID NO: 21) | preferably 54° C. |
| NC | AACTCTACGgggCTCTTCgA (SEQ ID NO: 22) | |
| Jsb | ggCTgCCTCgCCTgTgACAA (SEQ ID NO: 23) | 52-56° C. |
| Jsa | ggCTgCCCCgCCTgTgACAA (SEQ ID NO: 24) | preferably 54° C. |
| NC | gCCAgCCACgCgTgTCACTA (SEQ ID NO: 25) | |
| Lua | TCgCCCCCgCCTAgCCTC (SEQ ID NO: 26) | 43-47° C. |
| Lub | TCgCCCCCACCTAgCCTC (SEQ ID NO: 27) | preferably 45° C. |
| NC | TAgCCTCCTCCAAgACTA (SEQ ID NO: 28) | |
| s | TAggAgAAACgggACAACTT (SEQ ID NO: 29) | 50-54° C. |
| S | AggAgAAATgggACAACTTg (SEQ ID NO: 30) | preferably 54° C. |
| NC | TCggATAAAAgAgACCACTg (SEQ ID NO: 31) | |
| Coa | AACCAgAHggCggTCCAggA (SEQ ID NO: 32) | 62-66° C. |
| Cob | CAACCAgACggTggTCCAgg (SEQ ID NO: 33) | preferably 64° C. |
| NC | AgCCACACTggggACCTggA (SEQ ID NO: 34) | |
| Fya | GAgACTATggTgCCAACCTg (SEQ ID NO: 35) | 52-56° C. |
| Fyb | TggAgACTATgATgCCAACC (SEQ ID NO: 36) | preferably 54° C. |
| NC | gAggCTATCCTgACAAgCTT (SEQ ID NO: 37) | |
| Jka | AgTAgATgTCCTCAAATg (SEQ ID NO: 38) | 37-40° C. |
| Jkb | AgTAgATgTTCTCAAATg (SEQ ID NO: 39) | preferably 37° C. |
| NC | CgTggATTTCTTCAgAgg (SEQ ID NO: 40) | | d) fluorescence detection with a flow cytometry-based instrument, by detecting the fluorescence emitted by the specific microspheres preferably using a Luminex 100 instrument. FIG. 1 shows an example of the instrument software after fluorescence analysis of the samples.

The method adopted avails of the Luminex Xmap™ system as it uses an array of fluorescent microspheres covalently coupled in the laboratory with the specific complementary probes for the analysis of the polymorphisms of the above erythrocyte systems and flow-cytometer Luminex 100 (Luminex Corporation). The amplification of phase b) in the case of polymorphisms of the alleles Kpa/Kpb and Jsa/Jsb of the KELL system is preferably carried out by multiplex PCR.

The invention relates to a diagnostic kit for the identification and typing of at least one SNP of the erythrocyte systems, subject of the study, to identify the heterozygote and homozygote asset of samples, comprising the following components:

a) one or more pairs of primers for PCR amplification of the genomic locus comprising the SNP of the pair X selected from K/k, Kpa/Kpb, Jsa/Jsb, Lua/Lub, S/s, Coa/Cob, Fya/Fyb, Jka/Jkb, said pair of primers being selected from:

| Target alleles | Primer sequence (5'-3') |
|---|---|
| K/k | Fw: TTTAgTCCTCACTCCCATgCTTCC (SEQ ID NO: 1) |
| | Rw: TATCACACAggTgTCCTCTCTTCC (SEQ ID NO: 2) |
| Kpa/Kpb | Fw: TgAggCCAggAgAAAAgCA (SEQ ID NO: 3) |
| | Rw: TgACCATCTggAAgAgCTTgC (SEQ ID NO: 4) |
| Jsa/Jsb | Fw: AACTTTgCCATgCTCCTgg (SEQ ID NO: 5) |
| | Rw: gCCCTTgACACTTgCATACCT (SEQ ID NO: 6) |
| Lua/Lub | Fw: CTgAggAgCgCTgggACACCCgg (SEQ ID NO: 7) |
| | Rw: CCCCgggTgTCgTgCATT (SEQ ID NO: 8) |
| S/s | Fw: AAgACTgACACATTACCTCA (SEQ ID NO: 9) |
| | Rw: AACATACCTggTACAgTgAA (SEQ ID NO: 10) |
| Coa/Cob | Fw: TATAAATAggCCCAgCCCAg (SEQ ID NO: 11) |
| | Rw: CCAgCgACACCTTCACgTT (SEQ ID NO: 12) |
| Fya/Fyb | Fw: CTTCCggTgTAACTCTgATgg (SEQ ID NO: 13) |
| | Rw: CATCCAgCAGGTTACAggAgT (SEQ ID NO: 14) |
| Jka/Jkb | Fw: CATgCTgCCATAggATCATTgC (SEQ ID NO: 15) | b) at least one set of oligonucleotide probes as defined above, said probes being capable of hybridizing to said SNP.

Preferably, the set of primers as above defined used in multiplex PCR reactions according to the present invention are:

K5F/K6R, SsF/SsR, Duffy-F2/Duffy-R3 and JK-781-F3/JK-943-R3;

KpF/KpR, JsF/JsR, Lu91mF/Lu92R and CoF3/CoR3.

The present invention will now be described for illustrative and non-limiting purposes according to its preferred embodiments, with particular reference to the tables and enclosed FIGURE in which:

FIG. 1 shows the analysis of the Colton system where the fluorescence of the three microspheres of interest is analyzed (microspheres 74, 78, 80); the identifying codes of the samples are shown (column "sample"); the value obtained for each microsphere is the value of fluorescence emitted from the microsphere in turn coupled with the relative probes according to the invention; the column "events" refers to the number of total microspheres so that a minimum of 100 events (microspheres) are analyzed for each microsphere classification.

EXAMPLE

Genomic Typing of the Erythrocyte System X by Means of the Microarray System in Suspension which Uses Oligonucleotide Probes Complementary to the Specific SNP Coupled to an Array of Fluorescently-Labeled Microspheres Materials and Methods
Samples 7 mL of peripheral blood of the sample to be analyzed was collected in test-tubes containing the solution of EDTA as anticoagulant. The samples are preserved at −20° C. until the moment of testing. Aliquots of 200 µl of whole blood were used for DNA extraction with a commercial kit (QIAamp, Qiagen, Mississauga, Ontario, Canada), according to the instructions of the producer.

The samples tested are indicated in the relative tables (Tables 3-10).
Reagents

The polystyrene COOH xMAP Multi-Analyte microspheres were purchased from Luminex Corporation (Carboxylated Microspheres, L100-C1XX-01-Austin, Tex., USA).

The microspheres (5.6 µm in diameter) have carboxylic functional surface groups for the covalent bond with different analytes which, for the purposes of the present invention, are oligodeoxyribonucleotide probes amino-modified (AmC12) at the 5'-end. The polystyrene microspheres (commercially available) were classified by the producer by means of flow cytometry on account of the emission profile in the red/infrared wavelength of each microsphere classification.

100 microspheres are available as each specific region incorporates two fluorophores in a precise intensity ratio with each other which emit at different wavelengths (red and infrared) allowing them to be distinguished. Each distinct microsphere classification in fact has unique spectral characteristics and its own fluorescence intensity distribution which can be analyzed by the analysis instrument. Various regions were used in this study: see Table 2. All the different regions of microspheres numbered from 1 to 100 derive from the same starting material and differ only in terms of the quantities of red/infrared dyes.

2-N-morpholine ethanesulfonic acid (MES), 1-ethyl-3-(3-dimethylaminopropyl) carbodiimide hydrochloride (EDC), SAPE (100× stock 0.5 mg/ml Streptavidin-phycoerythrin) were obtained by Sigma, Pierce and One Lambda, Inc. respectively. The following buffers of One Lambda Inc, LAB-Type wash buffer and LABType sape buffer, were used respectively for the wash step after the hybridization phase and to dilute the SAPE stock.
Probe Design All the oligonucleotides used for the covalent coupling with the microspheres were modified at the 5'-end during the synthesis, by means of Amino-Modifier (AmC12). The polymorphism of the various systems studied in the design of the probes was preferably localized at or near the centre of the probe (specific polymorphism position—Table 2).

The probe length varies from 18 to 20 nucleotides and they are selected complementary to the sequence amplified by the biotinylated primer, on the basis of the genomic sequences deposited.

A set of probes is used for each system to be analyzed, comprising: two probes specific for the alleles of the system object of the study; one non-specific probe used as negative control (NC), as it has been specifically designed by changing, with respect to the sequence of the specific probe, six nucleotides so as not to have the possibility of matching with the target DNA. This probe is only used for evaluating the background fluorescence signal, controlling that all the wash steps have been carried out correctly and indirectly confirming the positive or negative signal of the specific probes:

Xa probe and Xb probe: from 18 to 20 nucleotides with AmC12 modification at the 5'-end: these are the specific probes for the polymorphism implied; the polymorphism of the various systems studied was preferably localized at or near the centre of the probe (specific polymorphism position—Table 2).

negative control probe (NC): from 18 to 20 nt with AmC12 modification at the 5'-end differing from the allele-specific probe by six nucleotide modifications so as to obtain a probe which can not hybridize to the specific polymorphism (ref. 13 Dunbar et al., 2000).

Various problems arose during the identification of these probes, which not all the hybridization temperature/PCR product/probe length combinations and polymorphism positions were able to overcome.

On the basis of the specific polymorphism of the alleles K/k, Kpa/Kpb, Jsa/Jsb, of the Kell system, each characterized by a single nucleotide change and by the relative genomic sequence deposited, in preliminary experiments, it was possible to identify the complementary probes of 18 nt with the specific polymorphism in a central position and couple them to the development fluorescent microspheres (L100-CDEV1-01 (Luminex)). The hybridization temperature used for the preliminary experiments was 45° C.

The following results were obtained:
K/k: the 18 nt probes, central polymorphism and PCR product obtained from a pair of primers described in literature (Lee, 1997) gave good specificity results in the typing of the samples tested with known serological typing, effected at a temperature of 45° C.
Kpa/Kpb: the 18 nt probes, central polymorphism and PCR product obtained from a pair of primers described in literature (ref. 16 Lee, 1997) gave no hybridization signal at a temperature of 45° C.

Further hybridization experiments were then effected varying only the hybridization temperature (between 50° C. and 54° C.) and maintaining the same probes and the same PCR product. Even the temperature of 37° C. did not allow the specific alleles to be distinguished.

At this point the PCR product was modified by designing, with the programs available (Primer Express, Applied Biosystems; OligoAnalyzer 3.0, Integrated DNA Technologies) new pairs of primers to shorten the final amplified product, thus favoring the hybridization phase (ref. 14 Dunbar et al., 2005). 20 nt probes were used with the position of the polymorphism adjusted, i.e. no longer located only at the center of the probe sequence.

The results show a specific signal which can be obtained by changing both the PCR product and the length of the probes at a certain temperature (54° C.).

Once the suitable combination for obtaining a high specificity had been found, the probes were coupled to the xMAP® Multi-Analyte microspheres (L100-C1XX01 COOH). Duffy system (Fya/Fyb) and Colton system (Coa/Cob): the 20 nt probes, polymorphism not only in a central position and PCR product obtained from a pair of primers designed directly with computerized programs did not give good results in terms of specificity in the hybridization phase carried out at temperatures ranging from 45° C. to 54° C.

In this case the PCR product was amplified using the primer pairs according to the invention, i.e. different primers were designed.

In order to distinguish the allele Coa, two 20 nt probes were used with the polymorphism of interest situated in a different position. After various tests at different temperatures, specific results were obtained with the sequence indicated in Table 2. MNS system (S/s): of the pair of primers for the amplification, only the specific sequence of the Forward primer (SsF) was obtained from literature (ref. 17 Hashmi et al., 2005). The Reverse primer was designed ex novo with the help of computerized programs, as described above. 20 nt probes were obtained, with the polymorphism at the center of the specific probes; in addition, for the allele s, 18 nt, 19 nt and 21 nt probes were also tested at various temperatures.

A specific distinguishing signal was obtained in the hybridization phase with the 20 nt probe at a temperature of 54° C. Lutheran System (Lua/Lub): Only the Reverse primer sequence described in literature was used for the specific amplification phase (Elnemer et al., 1997). The Forward primer was decided ex novo. 18 nt and 20 nt probes were used with the polymorphism at the center.

A specific signal was obtained in the hybridization phase at a temperature of 45° C. with 18 nt probes.

In order to obtain a specific hybridization at a temperature of 54° C. we also tried to use 20 nt probes but without any results.

Coupling of the Oligonucleotide Probes to the Fluorescently-Labeled Microspheres The various oligonucleotide probes modified at the 5'-end were conjugated, in separate reactions, with different classifications of carboxylated microspheres, according to the coupling protocol suggested by Luminex Corporation (Oligonucleotide Coupling Protocol).

An aliquot of each specific region containing $5 \times 10^6$ microspheres was microcentrifuged at 10,000 rpm for 2 minutes, the supernatant removed and the pellet resuspended in 50 µl of MES buffer 0.1 M, at pH 4.5. 0.2 nanomoles of amino-modified oligonucleotide probes were then added to the mixture.

An aqueous solution of 1-ethyl-3-(3-dimethylaminopropyl-carbodiimide HCl (EDC; 10 mg/ml) was then added to the mixture of microspheres/oligonucleotides and the resulting mixture was incubated at room temperature for 30 minutes in the dark. The addition of EDC and the incubation were repeated one more time. After a total incubation of 1 hour, the microspheres were washed with 1 ml of Tween-20 at 0.02%. The wash solution was removed by centrifugation, the wash step was repeated with 1 ml of SDS at 0.1% and the final mixture was resuspended in 100 µl of TE (Elution Buffer-QIAGEN), at pH 8 and preserved in the dark at 4° C. Before use, the microspheres were brought to room temperature for 5 minutes. The coupled microspheres, thus obtained, have an expected theoretic concentration of 50,000 microspheres/µl.

Amplification of Target DNA

The primers used for the amplification of all the systems in question are described in Table 1. The primers were used for the amplification of the specific locus under examination.

At least one primer of each primer pair was synthesized with Biotin TEG modification at the 5'-end, to label the target strand of the amplicon and detect hybridization of the specific probe with the target DNA, according to the indications of Luminex Corporation (synthesis and purification and modification of primers and probes by Primm).

The PCR was carried out with 0.5 µM of primer, 2-0.5 µL of genomic DNA (25-100 ng), 0.2 mM of dNTP, 1 mM of $MgCl_2$ (from 25 mM Applied Biosystem), 1×PCR Buffer (from 10× Applied Biosystem) and 0.5 U of Taq (GoTaq Promega). The final reaction volume is equal to 20 µl.

Mastercycler epgradient S (Eppendorf) was used for the thermal cycles using the following parameters: 2 minutes of initial DNA denaturation at 94° C., followed by 35 cycles at 94° C. for 20 seconds, 60° C. for 20 seconds, 72° C. for 30 seconds, with a final elongation phase at 72° C. for 5 minutes. The amplification products obtained can be visualized by electrophoresis on agarose gel at 2%.

Multiplex PCR Reactions

The authors set up 2 multiplex PCR reactions, in order to minimize laboriousness and hands-on time. PCRs were divided in two separate multiplex reactions: PCR (I) and PCR (II) (see Table below) on the basis of the frequency of use in the Laboratory and, therefore, the utility of the reactions, i.e. PCR (I) amplifies the systems for which samples are tested for on a routine basis; PCR (II) amplifies those systems that are tested for less frequently.

| Target alleles | Primer sequence (5'-3') |
|---|---|
| K/k<br>PCR (I) | Fw: TTTAgTCCTCACTCCCATgCTTCC<br>Rw: TATCACACAggTgTCCTCTCTTCC |
| Kpa/Kpb<br>PCR (II) | Fw: TgAggCCAggAgAAAAgCA<br>Rw: TgACCATCTggAAgAgCTTgC |
| Jsa/Jsb<br>PCR (II) | Fw: AACTTTgCCATgCTCCTgg<br>Rw: gCCCTTgACACTTgCATACCT |
| Lua/Lub<br>PCR (II) | Fw: CTgAggAgCgCTgggACACCCgg<br>Rw: CCCCgggTgTCgTgCATT |
| S/s<br>PCR (I) | Fw: AAgACTgACACATTACCTCA<br>Rw: AACATACCTggTACAgTgAA |
| Coa/Cob<br>PCR (II) | Fw: TATAAATAggCCCAgCCCAg<br>Rw: CCAgCgACACCTTCACgTT |
| Fya/Fyb<br>PCR (I) | Fw: CTTCCggTgTAACTCTgATgg<br>Rw: CATCCAgCAggTTACAggAgT |
| Jka/Jkb<br>PCR (I) | Fw: CATgCTgCCATAggATCATTgC<br>Rw: gAgCCAggAggTgggTTTgC |

The PCR is carried out with 0.3 µM of each primer, 4 µL of genomic DNA (100-400 ng), 0.2 mM of dNTP, 1.5 mM of $MgCl_2$ (from 25 mM Applied Biosystem), 1.5×PCR Buffer (from 10× Applied Biosystem) and 4 U of Taq (GoTaq Promega). The final reaction volume is equal to 50 µl. PCR parameters remain the same as for the single PCR reactions.

Hybridization

After the DNA amplification, 4 µl from each amplification reaction were transferred to 96-well microplates and diluted with 13 µl of TE Buffer. They were then sealed with adhesive film and heat denatured at 99° C. for 10 minutes with the use of a preheated thermal cycler.

The hybridization of the PCR products with the three probes for each system object of the study (two specific probes and a negative control) is effected by diluting the single probes, in the hybridization buffer supplied by One Lambda, Inc. LABType hybridization buffer), at a final concentration of 150 microspheres per microliter. The coupled microspheres, as described above, have a theoretical recovery of 50,000 microspheres per microliter.

After denaturation of the PCR products, 33 µl of microspheres diluted in hybridization solution, are added to each sample.

The samples were mixed and the microplate rapidly transferred to the thermal cycler preheated to the specific optimal hybridization temperature for each system as indicated in Table 2.

The hybridization is carried out for 15 minutes and immediately afterwards 100 μl of wash buffer are added (LABType wash buffer—One lambda Inc.).

The wash steps were carried out at room temperature by centrifugation (2,800 rpm for 5 minutes) with elimination of the supernatant by manual inversion of the plate. The samples are washed for a total of three times.

The samples are subsequently incubated for 5 minutes, at the same hybridization temperature, with 50 μl of a freshly prepared solution of 1×SAPE (0.5 mg/l streptavidin-R-phycoerythrin) in a dilution buffer supplied by One Lambda Inc. (LABType SAPE-Buffer).

At the end of the incubation, 100 μl of LABType wash buffer were rapidly added to each well (One Lambda, Inc). The microspheres were re-pelleted by centrifugation and the supernatant removed by inversion. Each sample was then resuspended in 80 μl of Sheath Fluid buffer supplied by Luminex. The plate was ready to be analyzed at the flow-cytometer-based instrument.

If it is not possible to analyze the samples immediately, the analysis plate can be preserved at +4° C. in the dark, up to a maximum of 24 hours.

Data Acquisition and Analysis

The samples were analyzed using a LAB Scan™100 (Luminex Corporation, Austin, Tex.).

The instrument is equipped with two laser sources of which one is a 635-nm red diode laser which excites the red and infrared fluorochromes and the other a 532-nm laser which excites the phycoerythrin (PE) reporter fluorochrome.

Each microsphere has a unique spectral address which can be identified by the instrument.

Two parameters, the count and median fluorescence intensity (MFI) are monitored for each data acquisition.

The count for each microsphere (single specific region) should be at least 100. The median fluorescence intensity (MFI) represents the average reporter fluorescence for the counted spheres, as previously described.

Allelic Ratio Determination:

The fluorescence intensity, generated by Luminex software, represents the MFI of each microsphere (or probe coupled with the microsphere) for each sample.

For each system studied, the allelic ratio was calculated in order to obtain a numerical value which, when analyzed on the basis of the reference threshold value, allows to distinguish between homozygote samples for each allele or heterozygote samples as indicated in Tables 3-10 (ref. 7 Beiboer et al. 2005).

In order to define the allelic ratio for each system, samples with a known typing obtained with hemagglutination and/or PCR-SSP, were tested.

The ratio value is obtained for each system from the ratio between the median fluorescence intensity (MFI) of the probe Xa, intended as being the most frequent allele in the Caucasian population, and the MFI sum of both alleles (Xa and Xb) of the system implied, as indicated in the following formula:

$$(MFI_a - MFI_{NC})/(MFI_a - MFI_{NC} + MFI_b - MFI_{NC})$$

The allele-specific MFI values minus the MFI value generated by the negative control (NC) probe are used in the formula for each sample. On the basis of the samples tested, it was possible to define an allelic ratio for each system. The data obtained are indicated in Tables 3-10 and in the cumulative Table 11 hereunder.

The raw fluorescence data registered by the instrument are then processed. In this case, in the analysis program created in Excel, the necessary mathematical formulae were established for automatically obtaining, for each specific probe (allele Xa and allele Xb), the fluorescence values minus the negative control value (for example, MFI probe Xa-MFI NC probe). This corrected MFI value is then used for calculating the allelic ratio of each single sample as previously described. An example of the spreadsheet form prepared in Excel for the data analysis is provided hereunder.

| Worksheet: | | | | Date: | | | |
|---|---|---|---|---|---|---|---|
| | | MFI | | $MFI_{Allele^-}$ | Allele | | |
| | S | s | NC | $MFI_{NC}$ | ratio | | |
| ID | 084 | 085 | 087 | S | s | s/(S + s) | Genotyping |
| 1A  144597 | | | | | | | |
| 1B  144596 | | | | | | | |
| 1C  144595 | | | | | | | |
| 1D  144594 | | | | | | | |
| 1E  144591 | | | | | | | |
| 1F  144590 | | | | | | | |
| 1G  144589 | | | | | | | |
| 1H  144588 | | | | | | | |

In formulating the table, the automatic conclusion of the typing was based on the reference allelic ratios. The typing cannot be automatically concluded if the allelic ratio obtained does not fall within the cutoff ranges established. In this case an automatic warning message appears.

The results obtained for each sample are also confirmed only if the fluorescence produced by the negative control probe does not exceed the value of 100 and if the sum of the fluorescence values of the specific probes is higher than four times the negative control value of the sample ($MFI_a + MFI_b > 4 \times MFI_{NC}$). These formulae were also included in Excel.

The data analysis is easy, rapid and does not require complicated application software.

A list of the tables (3-10) of the allelic ratios obtained from the single samples tested is provided below, whereas Table 11 indicates the allelic ratio values used as reference (cutoff) range, obtained from the average of the ratios of the single samples plus and/or minus two standard deviations.

The allelic ratios of the single samples:

TABLE 3

| Nr. | Allelic ratio a/(a + b) | Genotype | |
|---|---|---|---|
| 1 | 1.000 | Coa/Coa | Coa/Coa > 0.941 |
| 2 | 1.000 | Coa/Coa | |
| 3 | 0.995 | Coa/Coa | |
| 4 | 0.992 | Coa/Coa | |
| 5 | 0.990 | Coa/Coa | |
| 6 | 0.989 | Coa/Coa | |
| 7 | 0.984 | Coa/Coa | |
| 8 | 0.984 | Coa/Coa | |
| 9 | 0.984 | Coa/Coa | |
| 10 | 0.984 | Coa/Coa | |
| 11 | 0.984 | Coa/Coa | |
| 12 | 0.980 | Coa/Coa | |
| 13 | 0.980 | Coa/Coa | |
| 14 | 0.979 | Coa/Coa | |
| 15 | 0.978 | Coa/Coa | |
| 16 | 0.976 | Coa/Coa | |
| 17 | 0.976 | Coa/Coa | |
| 18 | 0.976 | Coa/Coa | |

TABLE 3-continued

| Nr. | Allelic ratio a/(a + b) | Genotype | |
|---|---|---|---|
| 19 | 0.975 | Coa/Coa | |
| 20 | 0.973 | Coa/Coa | |
| 21 | 0.973 | Coa/Coa | |
| 22 | 0.972 | Coa/Coa | |
| 23 | 0.971 | Coa/Coa | |
| 24 | 0.971 | Coa/Coa | |
| 25 | 0.970 | Coa/Coa | |
| 26 | 0.970 | Coa/Coa | |
| 27 | 0.969 | Coa/Coa | |
| 28 | 0.968 | Coa/Coa | |
| 29 | 0.968 | Coa/Coa | |
| 30 | 0.967 | Coa/Coa | |
| 31 | 0.967 | Coa/Coa | |
| 32 | 0.966 | Coa/Coa | |
| 33 | 0.966 | Coa/Coa | |
| 34 | 0.966 | Coa/Coa | |
| 35 | 0.965 | Coa/Coa | |
| 36 | 0.965 | Coa/Coa | |
| 37 | 0.965 | Coa/Coa | |
| 38 | 0.964 | Coa/Coa | |
| 39 | 0.964 | Coa/Coa | |
| 40 | 0.963 | Coa/Coa | |
| 41 | 0.963 | Coa/Coa | |
| 42 | 0.963 | Coa/Coa | |
| 43 | 0.962 | Coa/Coa | |
| 44 | 0.962 | Coa/Coa | |
| 45 | 0.962 | Coa/Coa | |
| 46 | 0.961 | Coa/Coa | |
| 47 | 0.961 | Coa/Coa | |
| 48 | 0.960 | Coa/Coa | |
| 49 | 0.960 | Coa/Coa | |
| 50 | 0.959 | Coa/Coa | |
| 51 | 0.958 | Coa/Coa | |
| 52 | 0.958 | Coa/Coa | |
| 53 | 0.958 | Coa/Coa | |
| 54 | 0.958 | Coa/Coa | |
| 55 | 0.958 | Coa/Coa | |
| 56 | 0.956 | Coa/Coa | |
| 57 | 0.954 | Coa/Coa | |
| 58 | 0.954 | Coa/Coa | |
| 59 | 0.950 | Coa/Coa | |
| 60 | 0.948 | Coa/Coa | |
| 61 | 0.946 | Coa/Coa | |
| 62 | 0.944 | Coa/Coa | |
| 63 | 0.923 | Coa/Coa | |
| 64 | 0.747 | Coa/Cob | 0.652 < Coa/Cob < 0.754 |
| 65 | 0.723 | Coa/Cob | |
| 66 | 0.717 | Coa/Cob | |
| 67 | 0.712 | Coa/Cob | |
| 68 | 0.704 | Coa/Cob | |
| 69 | 0.701 | Coa/Cob | |
| 70 | 0.690 | Coa/Cob | |
| 71 | 0.675 | Coa/Cob | |
| 72 | 0.663 | Coa/Cob | |
| 73 | 0.106 | Cob/Cob | Cob/Cob < 0.116 |
| 74 | 0.009 | Cob/Cob | |
| 75 | 0.007 | Cob/Cob | |
| 76 | 0.002 | Cob/Cob | |
| 77 | 0.002 | Cob/Cob | |

TABLE 4

| Nr. | Allelic ratio b/(a + b) | Genotype | |
|---|---|---|---|
| 1 | 0.996 | Fyb/Fyb | Fyb/Fyb > 0.931 |
| 2 | 0.996 | Fyb/Fyb | |
| 3 | 0.996 | Fyb/Fyb | |
| 4 | 0.994 | Fyb/Fyb | |
| 5 | 0.993 | Fyb/Fyb | |
| 6 | 0.992 | Fyb/Fyb | |
| 7 | 0.992 | Fyb/Fyb | |
| 8 | 0.991 | Fyb/Fyb | |
| 9 | 0.990 | Fyb/Fyb | |
| 10 | 0.986 | Fyb/Fyb | |
| 11 | 0.985 | Fyb/Fyb | |
| 12 | 0.984 | Fyb/Fyb | |
| 13 | 0.984 | Fyb/Fyb | |
| 14 | 0.983 | Fyb/Fyb | |
| 15 | 0.981 | Fyb/Fyb | |
| 16 | 0.981 | Fyb/Fyb | |
| 17 | 0.981 | Fyb/Fyb | |
| 18 | 0.980 | Fyb/Fyb | |
| 19 | 0.978 | Fyb/Fyb | |
| 20 | 0.976 | Fyb/Fyb | |
| 21 | 0.975 | Fyb/Fyb | |
| 22 | 0.974 | Fyb/Fyb | |
| 23 | 0.974 | Fyb/Fyb | |
| 24 | 0.974 | Fyb/Fyb | |
| 25 | 0.972 | Fyb/Fyb | |
| 26 | 0.971 | Fyb/Fyb | |
| 27 | 0.971 | Fyb/Fyb | |
| 28 | 0.970 | Fyb/Fyb | |
| 29 | 0.969 | Fyb/Fyb | |
| 30 | 0.968 | Fyb/Fyb | |
| 31 | 0.968 | Fyb/Fyb | |
| 32 | 0.967 | Fyb/Fyb | |
| 33 | 0.966 | Fyb/Fyb | |
| 34 | 0.965 | Fyb/Fyb | |
| 35 | 0.965 | Fyb/Fyb | |
| 36 | 0.965 | Fyb/Fyb | |
| 37 | 0.963 | Fyb/Fyb | |
| 38 | 0.960 | Fyb/Fyb | |
| 39 | 0.959 | Fyb/Fyb | |
| 40 | 0.958 | Fyb/Fyb | |
| 41 | 0.958 | Fyb/Fyb | |
| 42 | 0.956 | Fyb/Fyb | |
| 43 | 0.953 | Fyb/Fyb | |
| 44 | 0.949 | Fyb/Fyb | |
| 45 | 0.948 | Fyb/Fyb | |
| 46 | 0.946 | Fyb/Fyb | |
| 47 | 0.945 | Fyb/Fyb | |
| 48 | 0.944 | Fyb/Fyb | |
| 49 | 0.939 | Fyb/Fyb | |
| 50 | 0.935 | Fyb/Fyb | |
| 51 | 0.930 | Fyb/Fyb | |
| 52 | 0.929 | Fyb/Fyb | |
| 53 | 0.920 | Fyb/Fyb | |
| 54 | 0.888 | Fya/Fyb | 0.752 < Fya/Fyb < 0.902 |
| 55 | 0.888 | Fya/Fyb | |
| 56 | 0.871 | Fya/Fyb | |
| 57 | 0.868 | Fya/Fyb | |
| 58 | 0.862 | Fya/Fyb | |
| 59 | 0.862 | Fya/Fyb | |
| 60 | 0.860 | Fya/Fyb | |
| 61 | 0.854 | Fya/Fyb | |
| 62 | 0.851 | Fya/Fyb | |
| 63 | 0.841 | Fya/Fyb | |
| 64 | 0.831 | Fya/Fyb | |
| 65 | 0.819 | Fya/Fyb | |
| 66 | 0.817 | Fya/Fyb | |
| 67 | 0.816 | Fya/Fyb | |
| 68 | 0.812 | Fya/Fyb | |
| 69 | 0.808 | Fya/Fyb | |
| 70 | 0.792 | Fya/Fyb | |
| 71 | 0.788 | Fya/Fyb | |
| 72 | 0.787 | Fya/Fyb | |
| 73 | 0.787 | Fya/Fyb | |
| 74 | 0.779 | Fya/Fyb | |
| 75 | 0.772 | Fya/Fyb | |
| 76 | 0.772 | Fya/Fyb | |
| 77 | 0.070 | Fya/Fya | Fya/Fya < 0.050 |
| 78 | 0.049 | Fya/Fya | |
| 79 | 0.041 | Fya/Fya | |
| 80 | 0.040 | Fya/Fya | |
| 81 | 0.034 | Fya/Fya | |
| 82 | 0.032 | Fya/Fya | |
| 83 | 0.029 | Fya/Fya | |
| 84 | 0.025 | Fya/Fya | |
| 85 | 0.025 | Fya/Fya | |
| 86 | 0.024 | Fya/Fya | |

TABLE 4-continued

| Nr. | Allelic ratio b/(a + b) | Genotype | | |
|---|---|---|---|---|
| 87 | 0.024 | Fya/Fya | | |
| 88 | 0.018 | Fya/Fya | | |
| 89 | 0.017 | Fya/Fya | | |
| 90 | 0.016 | Fya/Fya | | |
| 91 | 0.016 | Fya/Fya | | |
| 92 | 0.016 | Fya/Fya | | |
| 93 | 0.016 | Fya/Fya | | |
| 94 | 0.015 | Fya/Fya | | |
| 95 | 0.014 | Fya/Fya | | |
| 96 | 0.013 | Fya/Fya | | |
| 97 | 0.012 | Fya/Fya | | |
| 98 | 0.010 | Fya/Fya | | |
| 99 | 0.009 | Fya/Fya | | |
| 100 | 0.007 | Fya/Fya | | |
| 101 | 0.007 | Fya/Fya | | |
| 102 | 0.006 | Fya/Fya | | |
| 103 | 0.006 | Fya/Fya | | |
| 104 | 0.002 | Fya/Fya | | |
| 105 | 0.002 | Fya/Fya | | |
| 106 | 0.000 | Fya/Fya | | |
| 107 | 0.000 | Fya/Fya | | |
| 108 | 0.000 | Fya/Fya | | |

TABLE 5

| Nr. | Allelic ratio a/(a + b) | Genotype | |
|---|---|---|---|
| 1 | 1.000 | Jka/Jka | Jka/Jka > 0.870 |
| 2 | 1.000 | Jka/Jka | |
| 3 | 1.000 | Jka/Jka | |
| 4 | 0.988 | Jka/Jka | |
| 5 | 0.975 | Jka/Jka | |
| 6 | 0.974 | Jka/Jka | |
| 7 | 0.960 | Jka/Jka | |
| 8 | 0.954 | Jka/Jka | |
| 9 | 0.942 | Jka/Jka | |
| 10 | 0.942 | Jka/Jka | |
| 11 | 0.939 | Jka/Jka | |
| 12 | 0.938 | Jka/Jka | |
| 13 | 0.934 | Jka/Jka | |
| 14 | 0.934 | Jka/Jka | |
| 15 | 0.930 | Jka/Jka | |
| 16 | 0.930 | Jka/Jka | |
| 17 | 0.924 | Jka/Jka | |
| 18 | 0.924 | Jka/Jka | |
| 19 | 0.923 | Jka/Jka | |
| 20 | 0.921 | Jka/Jka | |
| 21 | 0.921 | Jka/Jka | |
| 22 | 0.920 | Jka/Jka | |
| 23 | 0.920 | Jka/Jka | |
| 24 | 0.919 | Jka/Jka | |
| 25 | 0.917 | Jka/Jka | |
| 26 | 0.913 | Jka/Jka | |
| 27 | 0.913 | Jka/Jka | |
| 28 | 0.911 | Jka/Jka | |
| 29 | 0.910 | Jka/Jka | |
| 30 | 0.910 | Jka/Jka | |
| 31 | 0.909 | Jka/Jka | |
| 32 | 0.909 | Jka/Jka | |
| 33 | 0.907 | Jka/Jka | |
| 34 | 0.907 | Jka/Jka | |
| 35 | 0.906 | Jka/Jka | |
| 36 | 0.906 | Jka/Jka | |
| 37 | 0.902 | Jka/Jka | |
| 38 | 0.895 | Jka/Jka | |
| 39 | 0.873 | Jka/Jka | |
| 40 | 0.269 | Jka/Jkb | 0.175 < Jka/Jkb < 0.260 |
| 41 | 0.256 | Jka/Jkb | |
| 42 | 0.243 | Jka/Jkb | |
| 43 | 0.240 | Jka/Jkb | |
| 44 | 0.239 | Jka/Jkb | |
| 45 | 0.233 | Jka/Jkb | |
| 46 | 0.221 | Jka/Jkb | |

TABLE 5-continued

| Nr. | Allelic ratio a/(a + b) | Genotype | |
|---|---|---|---|
| 47 | 0.221 | Jka/Jkb | |
| 48 | 0.218 | Jka/Jkb | |
| 49 | 0.215 | Jka/Jkb | |
| 50 | 0.212 | Jka/Jkb | |
| 51 | 0.212 | Jka/Jkb | |
| 52 | 0.210 | Jka/Jkb | |
| 53 | 0.209 | Jka/Jkb | |
| 54 | 0.206 | Jka/Jkb | |
| 55 | 0.204 | Jka/Jkb | |
| 56 | 0.203 | Jka/Jkb | |
| 57 | 0.203 | Jka/Jkb | |
| 58 | 0.200 | Jka/Jkb | |
| 59 | 0.197 | Jka/Jkb | |
| 60 | 0.193 | Jka/Jkb | |
| 61 | 0.184 | Jka/Jkb | |
| 62 | 0.016 | Jkb/Jkb | Jkb/Jkb < 0.016 |
| 63 | 0.014 | Jkb/Jkb | |
| 64 | 0.014 | Jkb/Jkb | |
| 65 | 0.014 | Jkb/Jkb | |
| 66 | 0.013 | Jkb/Jkb | |
| 67 | 0.011 | Jkb/Jkb | |
| 68 | 0.010 | Jkb/Jkb | |
| 69 | 0.009 | Jkb/Jkb | |
| 70 | 0.009 | Jkb/Jkb | |
| 71 | 0.009 | Jkb/Jkb | |
| 72 | 0.009 | Jkb/Jkb | |
| 73 | 0.009 | Jkb/Jkb | |
| 74 | 0.008 | Jkb/Jkb | |
| 75 | 0.008 | Jkb/Jkb | |
| 76 | 0.007 | Jkb/Jkb | |
| 77 | 0.007 | Jkb/Jkb | |
| 78 | 0.004 | Jkb/Jkb | |
| 79 | 0.004 | Jkb/Jkb | |
| 80 | 0.001 | Jkb/Jkb | |
| 81 | 0.001 | Jkb/Jkb | |
| 82 | 0.001 | Jkb/Jkb | |
| 83 | 0.000 | Jkb/Jkb | |
| 84 | 0.000 | Jkb/Jkb | |
| 85 | 0.000 | Jkb/Jkb | |
| 86 | 0.000 | Jkb/Jkb | |
| 87 | 0.000 | Jkb/Jkb | |
| 88 | 0.000 | Jkb/Jkb | |
| 89 | 0.000 | Jkb/Jkb | |
| 90 | 0.000 | Jkb/Jkb | |
| 91 | 0.000 | Jkb/Jkb | |
| 92 | 0.000 | Jkb/Jkb | |
| 93 | 0.000 | Jkb/Jkb | |
| 94 | 0.000 | Jkb/Jkb | |

TABLE 6

| Nr. | Allelic ratio b/(a + b) | Genotype | |
|---|---|---|---|
| 1 | 1.000 | Jsb/Jsb | Jsb/Jsb > 0.831 |
| 2 | 1.000 | Jsb/Jsb | |
| 3 | 1.000 | Jsb/Jsb | |
| 4 | 1.000 | Jsb/Jsb | |
| 5 | 1.000 | Jsb/Jsb | |
| 6 | 1.000 | Jsb/Jsb | |
| 7 | 1.000 | Jsb/Jsb | |
| 8 | 1.000 | Jsb/Jsb | |
| 9 | 1.000 | Jsb/Jsb | |
| 10 | 1.000 | Jsb/Jsb | |
| 11 | 1.000 | Jsb/Jsb | |
| 12 | 0.993 | Jsb/Jsb | |
| 13 | 0.993 | Jsb/Jsb | |
| 14 | 0.991 | Jsb/Jsb | |
| 15 | 0.990 | Jsb/Jsb | |
| 16 | 0.988 | Jsb/Jsb | |
| 17 | 0.987 | Jsb/Jsb | |
| 18 | 0.986 | Jsb/Jsb | |
| 19 | 0.984 | Jsb/Jsb | |
| 20 | 0.983 | Jsb/Jsb | |

TABLE 6-continued

| Nr. | Allelic ratio b/(a + b) | Genotype | |
|---|---|---|---|
| 21 | 0.983 | Jsb/Jsb | |
| 22 | 0.979 | Jsb/Jsb | |
| 23 | 0.979 | Jsb/Jsb | |
| 24 | 0.978 | Jsb/Jsb | |
| 25 | 0.973 | Jsb/Jsb | |
| 26 | 0.973 | Jsb/Jsb | |
| 27 | 0.972 | Jsb/Jsb | |
| 28 | 0.972 | Jsb/Jsb | |
| 29 | 0.971 | Jsb/Jsb | |
| 30 | 0.967 | Jsb/Jsb | |
| 31 | 0.966 | Jsb/Jsb | |
| 32 | 0.964 | Jsb/Jsb | |
| 33 | 0.962 | Jsb/Jsb | |
| 34 | 0.960 | Jsb/Jsb | |
| 35 | 0.955 | Jsb/Jsb | |
| 36 | 0.953 | Jsb/Jsb | |
| 37 | 0.953 | Jsb/Jsb | |
| 38 | 0.949 | Jsb/Jsb | |
| 39 | 0.949 | Jsb/Jsb | |
| 40 | 0.949 | Jsb/Jsb | |
| 41 | 0.948 | Jsb/Jsb | |
| 42 | 0.946 | Jsb/Jsb | |
| 43 | 0.944 | Jsb/Jsb | |
| 44 | 0.940 | Jsb/Jsb | |
| 45 | 0.932 | Jsb/Jsb | |
| 46 | 0.931 | Jsb/Jsb | |
| 47 | 0.930 | Jsb/Jsb | |
| 48 | 0.929 | Jsb/Jsb | |
| 49 | 0.929 | Jsb/Jsb | |
| 50 | 0.923 | Jsb/Jsb | |
| 51 | 0.916 | Jsb/Jsb | |
| 52 | 0.908 | Jsb/Jsb | |
| 53 | 0.900 | Jsb/Jsb | |
| 54 | 0.899 | Jsb/Jsb | |
| 55 | 0.899 | Jsb/Jsb | |
| 56 | 0.897 | Jsb/Jsb | |
| 57 | 0.896 | Jsb/Jsb | |
| 58 | 0.894 | Jsb/Jsb | |
| 59 | 0.893 | Jsb/Jsb | |
| 60 | 0.893 | Jsb/Jsb | |
| 61 | 0.893 | Jsb/Jsb | |
| 62 | 0.891 | Jsb/Jsb | |
| 63 | 0.891 | Jsb/Jsb | |
| 64 | 0.887 | Jsb/Jsb | |
| 65 | 0.886 | Jsb/Jsb | |
| 66 | 0.885 | Jsb/Jsb | |
| 67 | 0.879 | Jsb/Jsb | |
| 68 | 0.877 | Jsb/Jsb | |
| 69 | 0.877 | Jsb/Jsb | |
| 70 | 0.875 | Jsb/Jsb | |
| 71 | 0.868 | Jsb/Jsb | |
| 72 | 0.857 | Jsb/Jsb | |
| 73 | 0.853 | Jsb/Jsb | |
| 74 | 0.852 | Jsb/Jsb | |
| 75 | 0.852 | Jsb/Jsb | |
| 76 | 0.845 | Jsb/Jsb | |
| 77 | 0.838 | Jsb/Jsb | |
| 78 | 0.835 | Jsb/Jsb | |
| 79 | 0.830 | Jsb/Jsb | |
| 80 | 0.828 | Jsb/Jsb | |
| 81 | 0.545 | Jsa/Jsb | 0.509 < Jsa/Jsb < 0.562 |
| 82 | 0.526 | Jsa/Jsb | |

TABLE 7

| Nr. | Allelic ratio k/(K + k) | Genotype | |
|---|---|---|---|
| 1 | 0.830 | kk | |
| 2 | 0.828 | kk | |
| 3 | 0.807 | kk | |
| 4 | 0.807 | kk | |
| 5 | 0.792 | kk | |
| 6 | 0.790 | kk | |
| 7 | 0.787 | kk | |
| 8 | 0.783 | kk | |
| 9 | 0.775 | kk | |
| 10 | 0.773 | kk | |
| 11 | 0.772 | kk | |
| 12 | 0.772 | kk | |
| 13 | 0.771 | kk | |
| 14 | 0.770 | kk | |
| 15 | 0.769 | kk | |
| 16 | 0.767 | kk | |
| 17 | 0.764 | kk | |
| 18 | 0.763 | kk | |
| 19 | 0.763 | kk | |
| 20 | 0.759 | kk | |
| 21 | 0.759 | kk | |
| 22 | 0.759 | kk | |
| 23 | 0.757 | kk | |
| 24 | 0.756 | kk | |
| 25 | 0.754 | kk | |
| 26 | 0.754 | kk | |
| 27 | 0.752 | kk | |
| 28 | 0.748 | kk | |
| 29 | 0.748 | kk | |
| 30 | 0.748 | kk | |
| 31 | 0.744 | kk | |
| 32 | 0.743 | kk | |
| 33 | 0.742 | kk | |
| 34 | 0.741 | kk | |
| 35 | 0.737 | kk | |
| 36 | 0.735 | kk | |
| 37 | 0.732 | kk | |
| 38 | 0.731 | kk | |
| 39 | 0.729 | kk | |
| 40 | 0.729 | kk | |
| 41 | 0.726 | kk | |
| 42 | 0.726 | kk | |
| 43 | 0.726 | kk | |
| 44 | 0.724 | kk | |
| 45 | 0.723 | kk | |
| 46 | 0.722 | kk | |
| 47 | 0.721 | kk | |
| 48 | 0.710 | kk | |
| 49 | 0.710 | kk | |
| 50 | 0.710 | kk | |
| 51 | 0.709 | kk | |
| 52 | 0.709 | kk | |
| 53 | 0.708 | kk | |
| 54 | 0.708 | kk | |
| 55 | 0.706 | kk | |
| 56 | 0.704 | kk | |
| 57 | 0.699 | kk | |
| 58 | 0.697 | kk | |
| 59 | 0.697 | kk | |
| 60 | 0.696 | kk | |
| 61 | 0.695 | kk | |
| 62 | 0.695 | kk | |
| 63 | 0.692 | kk | |
| 64 | 0.692 | kk | |
| 65 | 0.691 | kk | |
| 66 | 0.690 | kk | |
| 67 | 0.683 | kk | |
| 68 | 0.681 | kk | |
| 69 | 0.680 | kk | |
| 70 | 0.679 | kk | |
| 71 | 0.673 | kk | |
| 72 | 0.673 | kk | |
| 73 | 0.672 | kk | |
| 74 | 0.669 | kk | |
| 75 | 0.668 | kk | |
| 76 | 0.665 | kk | |
| 77 | 0.664 | kk | |
| 78 | 0.656 | kk | |
| 79 | 0.653 | kk | |
| 80 | 0.549 | kK | 0.502 < K/k < 0.550 |
| 81 | 0.537 | kK | |
| 82 | 0.535 | kK | |
| 83 | 0.531 | kK | |

TABLE 7-continued

| Nr. | Allelic ratio k/(K + k) | Genotype | |
|---|---|---|---|
| 84 | 0.531 | kK | |
| 85 | 0.527 | kK | |
| 86 | 0.521 | kK | |
| 87 | 0.520 | kK | |
| 88 | 0.518 | kK | |
| 89 | 0.517 | kK | |
| 90 | 0.504 | kK | |
| 91 | 0.025 | KK | K/K < 0.036 |
| 92 | 0.022 | KK | |
| 93 | 0.006 | KK | |
| 94 | 0.004 | KK | |

TABLE 8

| Nr. | Allelic ratio b/(b + a) | Genotype | |
|---|---|---|---|
| 1 | 0.953 | Kpb/Kpb | Kpb/Kpb > 0.867 |
| 2 | 0.951 | Kpb/Kpb | |
| 3 | 0.950 | Kpb/Kpb | |
| 4 | 0.947 | Kpb/Kpb | |
| 5 | 0.946 | Kpb/Kpb | |
| 6 | 0.945 | Kpb/Kpb | |
| 7 | 0.943 | Kpb/Kpb | |
| 8 | 0.943 | Kpb/Kpb | |
| 9 | 0.942 | Kpb/Kpb | |
| 10 | 0.942 | Kpb/Kpb | |
| 11 | 0.940 | Kpb/Kpb | |
| 12 | 0.939 | Kpb/Kpb | |
| 13 | 0.937 | Kpb/Kpb | |
| 14 | 0.934 | Kpb/Kpb | |
| 15 | 0.933 | Kpb/Kpb | |
| 16 | 0.932 | Kpb/Kpb | |
| 17 | 0.930 | Kpb/Kpb | |
| 18 | 0.929 | Kpb/Kpb | |
| 19 | 0.928 | Kpb/Kpb | |
| 20 | 0.928 | Kpb/Kpb | |
| 21 | 0.927 | Kpb/Kpb | |
| 22 | 0.926 | Kpb/Kpb | |
| 23 | 0.925 | Kpb/Kpb | |
| 24 | 0.925 | Kpb/Kpb | |
| 25 | 0.924 | Kpb/Kpb | |
| 26 | 0.923 | Kpb/Kpb | |
| 27 | 0.921 | Kpb/Kpb | |
| 28 | 0.921 | Kpb/Kpb | |
| 29 | 0.921 | Kpb/Kpb | |
| 30 | 0.919 | Kpb/Kpb | |
| 31 | 0.918 | Kpb/Kpb | |
| 32 | 0.916 | Kpb/Kpb | |
| 33 | 0.915 | Kpb/Kpb | |
| 34 | 0.915 | Kpb/Kpb | |
| 35 | 0.915 | Kpb/Kpb | |
| 36 | 0.914 | Kpb/Kpb | |
| 37 | 0.912 | Kpb/Kpb | |
| 38 | 0.912 | Kpb/Kpb | |
| 39 | 0.912 | Kpb/Kpb | |
| 40 | 0.911 | Kpb/Kpb | |
| 41 | 0.911 | Kpb/Kpb | |
| 42 | 0.911 | Kpb/Kpb | |
| 43 | 0.909 | Kpb/Kpb | |
| 44 | 0.909 | Kpb/Kpb | |
| 45 | 0.908 | Kpb/Kpb | |
| 46 | 0.908 | Kpb/Kpb | |
| 47 | 0.908 | Kpb/Kpb | |
| 48 | 0.905 | Kpb/Kpb | |
| 49 | 0.905 | Kpb/Kpb | |
| 50 | 0.905 | Kpb/Kpb | |
| 51 | 0.900 | Kpb/Kpb | |
| 52 | 0.897 | Kpb/Kpb | |
| 53 | 0.893 | Kpb/Kpb | |
| 54 | 0.893 | Kpb/Kpb | |
| 55 | 0.890 | Kpb/Kpb | |
| 56 | 0.890 | Kpb/Kpb | |
| 57 | 0.889 | Kpb/Kpb | |

TABLE 8-continued

| Nr. | Allelic ratio b/(b + a) | Genotype | |
|---|---|---|---|
| 58 | 0.888 | Kpb/Kpb | |
| 59 | 0.888 | Kpb/Kpb | |
| 60 | 0.888 | Kpb/Kpb | |
| 61 | 0.86 | Kpb/Kpb | |
| 62 | 0.882 | Kpb/Kpb | |
| 63 | 0.882 | Kpb/Kpb | |
| 64 | 0.882 | Kpb/Kpb | |
| 65 | 0.880 | Kpb/Kpb | |
| 66 | 0.872 | Kpb/Kpb | |
| 67 | 0.862 | Kpb/Kpb | |
| 68 | 0.862 | Kpb/Kpb | |
| 69 | 0.853 | Kpb/Kpb | |
| 70 | 0.357 | Kpa/Kpb | 0.342 < Kpa/Kpb < 0.364 |
| 71 | 0.349 | Kpa/Kpb | |
| 72 | 0.025 | Kpa/Kpa | Kpa/Kpa < 0.031 |
| 73 | 0.005 | Kpa/Kpa | |
| 74 | 0.004 | Kpa/Kpa | |
| 75 | 0.003 | Kpa/Kpa | |

TABLE 9

| Nr. | Allelic ratio s/(S + s) | Genotype | |
|---|---|---|---|
| 1 | 1.000 | ss | s/s > 0.860 |
| 2 | 0.992 | ss | |
| 3 | 0.990 | ss | |
| 4 | 0.989 | ss | |
| 5 | 0.981 | ss | |
| 6 | 0.979 | ss | |
| 7 | 0.979 | ss | |
| 8 | 0.978 | ss | |
| 9 | 0.977 | ss | |
| 10 | 0.976 | ss | |
| 11 | 0.972 | ss | |
| 12 | 0.967 | ss | |
| 13 | 0.964 | ss | |
| 14 | 0.961 | ss | |
| 15 | 0.958 | ss | |
| 16 | 0.956 | ss | |
| 17 | 0.955 | ss | |
| 18 | 0.954 | ss | |
| 19 | 0.951 | ss | |
| 20 | 0.948 | ss | |
| 21 | 0.947 | ss | |
| 22 | 0.946 | ss | |
| 23 | 0.945 | ss | |
| 24 | 0.944 | ss | |
| 25 | 0.944 | ss | |
| 26 | 0.943 | ss | |
| 27 | 0.942 | ss | |
| 28 | 0.941 | ss | |
| 29 | 0.939 | ss | |
| 30 | 0.938 | ss | |
| 31 | 0.936 | ss | |
| 32 | 0.936 | ss | |
| 33 | 0.932 | ss | |
| 34 | 0.929 | ss | |
| 35 | 0.928 | ss | |
| 36 | 0.925 | ss | |
| 37 | 0.922 | ss | |
| 38 | 0.920 | ss | |
| 39 | 0.918 | ss | |
| 40 | 0.909 | ss | |
| 41 | 0.909 | ss | |
| 42 | 0.908 | ss | |
| 43 | 0.895 | ss | |
| 44 | 0.887 | ss | |
| 45 | 0.885 | ss | |
| 46 | 0.883 | ss | |
| 47 | 0.879 | ss | |
| 48 | 0.879 | ss | |
| 49 | 0.878 | ss | |

TABLE 9-continued

| Nr. | Allelic ratio s/(S + s) | Genotype | |
|---|---|---|---|
| 50 | 0.878 | ss | |
| 51 | 0.880 | ss | |
| 52 | 0.073 | sS | 0.014 < S/s < 0.059 |
| 53 | 0.052 | sS | |
| 54 | 0.050 | sS | |
| 55 | 0.047 | sS | |
| 56 | 0.045 | sS | |
| 57 | 0.038 | sS | |
| 58 | 0.036 | sS | |
| 59 | 0.035 | sS | |
| 60 | 0.034 | sS | |
| 61 | 0.034 | sS | |
| 62 | 0.034 | sS | |
| 63 | 0.033 | sS | |
| 64 | 0.033 | sS | |
| 65 | 0.032 | sS | |
| 66 | 0.032 | sS | |
| 67 | 0.032 | sS | |
| 68 | 0.032 | sS | |
| 69 | 0.032 | sS | |
| 70 | 0.031 | sS | |
| 71 | 0.030 | sS | |
| 72 | 0.030 | sS | |
| 73 | 0.029 | sS | |
| 74 | 0.016 | sS | |
| 75 | 0.009 | SS | S/S < 0.009 |
| 76 | 0.008 | SS | |
| 77 | 0.007 | SS | |
| 78 | 0.007 | SS | |
| 79 | 0.006 | SS | |
| 80 | 0.006 | SS | |
| 81 | 0.005 | SS | |
| 82 | 0.005 | SS | |
| 83 | 0.004 | SS | |
| 84 | 0.004 | SS | |
| 85 | 0.004 | SS | |
| 86 | 0.004 | SS | |
| 87 | 0.003 | SS | |
| 88 | 0.003 | SS | |
| 89 | 0.002 | SS | |
| 90 | 0.002 | SS | |
| 91 | 0.002 | SS | |
| 92 | 0.002 | SS | |
| 93 | 0.002 | SS | |
| 94 | 0.001 | SS | |
| 95 | 0.001 | SS | |
| 96 | 0.001 | SS | |
| 97 | 0.000 | SS | |

TABLE 10

| Nr. | Allelic ratio b/(a + b) | Genotype | |
|---|---|---|---|
| 1 | 1.000 | Lub/Lub | Lub/Lub < 0.880 |
| 2 | 1.000 | Lub/Lub | |
| 3 | 1.000 | Lub/Lub | |
| 4 | 1.000 | Lub/Lub | |
| 5 | 1.000 | Lub/Lub | |
| 6 | 1.000 | Lub/Lub | |
| 7 | 1.000 | Lub/Lub | |
| 8 | 0.998 | Lub/Lub | |
| 9 | 0.986 | Lub/Lub | |
| 10 | 0.985 | Lub/Lub | |
| 11 | 0.980 | Lub/Lub | |
| 12 | 0.970 | Lub/Lub | |
| 13 | 0.969 | Lub/Lub | |
| 14 | 0.958 | Lub/Lub | |
| 15 | 0.957 | Lub/Lub | |
| 16 | 0.956 | Lub/Lub | |
| 17 | 0.956 | Lub/Lub | |
| 18 | 0.950 | Lub/Lub | |
| 19 | 0.949 | Lub/Lub | |
| 20 | 0.947 | Lub/Lub | |
| 21 | 0.947 | Lub/Lub | |
| 22 | 0.947 | Lub/Lub | |
| 23 | 0.947 | Lub/Lub | |
| 24 | 0.946 | Lub/Lub | |
| 25 | 0.945 | Lub/Lub | |
| 26 | 0.944 | Lub/Lub | |
| 27 | 0.942 | Lub/Lub | |
| 28 | 0.941 | Lub/Lub | |
| 29 | 0.940 | Lub/Lub | |
| 30 | 0.940 | Lub/Lub | |
| 31 | 0.939 | Lub/Lub | |
| 32 | 0.938 | Lub/Lub | |
| 33 | 0.936 | Lub/Lub | |
| 34 | 0.933 | Lub/Lub | |
| 35 | 0.932 | Lub/Lub | |
| 36 | 0.930 | Lub/Lub | |
| 37 | 0.928 | Lub/Lub | |
| 38 | 0.927 | Lub/Lub | |
| 39 | 0.925 | Lub/Lub | |
| 40 | 0.922 | Lub/Lub | |
| 41 | 0.912 | Lub/Lub | |
| 42 | 0.910 | Lub/Lub | |
| 43 | 0.907 | Lub/Lub | |
| 44 | 0.907 | Lub/Lub | |
| 45 | 0.901 | Lub/Lub | |
| 46 | 0.901 | Lub/Lub | |
| 47 | 0.899 | Lub/Lub | |
| 48 | 0.898 | Lub/Lub | |
| 49 | 0.892 | Lub/Lub | |
| 50 | 0.872 | Lub/Lub | |
| 51 | 0.651 | Lua/Lub | 0.540 < Lua/Lub < 0.695 |
| 52 | 0.627 | Lua/Lub | |
| 53 | 0.575 | Lua/Lub | |
| 54 | 0.301 | Lua/Lua | Lua/Lua < 0.307 |
| 55 | 0.291 | Lua/Lua | |
| 56 | 0.289 | Lua/Lua | |

TABLE 11

| System | Allelic ratio for the determination of genotype* | | |
|---|---|---|---|
| MNS | s/s > 0.860 | 0.059 > S/s > 0.014 | S/S < 0.009 |
| Duffy | $Fy^b/Fy^b$ > 0.931 | 0.902 > $Fy^a/Fy^b$ > 0.752 | $Fy^a/Fy^a$ > 0.050 |
| Kell | $Kp^b/Kp^b$ > 0.867 | 0.364 > $KP^a/KP^b$ > 0.342 | $Kp^a/Kp^a$ < 0.031 |
| | $Js^b/Js^b$ > 0.831 | 0.562 > $Js^a/Js^b$ > 0.509 | $Js^a/Js^a$ < ND** |
| | k/k > 0.647 | 0.550 > K/k > 0.502 | K/K < 0.036 |
| Lu | $Lu^b/Lu^b$ > 0.880 | 0.695 > $Lu^a/Lu^b$ > 0.540 | $Lu^a/Lu^a$ < 0.307 |
| Co | $Co^a/Co^a$ > 0.941 | 0.754 > $Co^a/Co^b$ > 0.652 | $Co^b/Co^b$ < 0.116 |
| Jk | $Jk^a/Jk^a$ > 0.870 | 0.260 > $Jk^a/Jk^b$ > 0.175 | $Jk^b/Jk^b$ < 0.016 |

*reference ranges obtained from the average of the allelic ratios of the single samples plus and/or minus two standard deviations
**no available Jsa/Jsa samples

BIBLIOGRAPHY

1) Castilho L. et al. Transfusion 2002; 42(2):232-240
2) Montalvo L. et al. Transfusion 2004; 44(5):694-702
3) Reid M E. Vox Sanguinis 2002; 83(1): 91-93
4) Ferri G. et al. Journal of Forensic Sciences 2006; 51:357-360
5) Denomme G. et al. Transfusion 2005; 45: 660-666
6) Petrik J. Vox Sanguinis 2001; 80: 1-11
7) Beiboer S. et al. Transfusion 2005; 45:667-679
8) Kellar K L. et al., J. Immunol. Methods 2003; 279(1-2): 277-285
9) Kettman J R et al. Cytometry 1998; 33(2): 234-243
10) Fulton R F et al. Clinical Chemistry 1997; 43(9): 1749-1756
11) Earley M C et al. Cytometry 2002; 50(5): 239-242

12) Colinas R F et al. Clinical Chemistry 2000; 46 (7): 996-998
13) Dunbar S A et al. Clinical chemistry 2000; 46 1498-1500
14) Dunbar S A et al. 2005; Methods Mol Med 114: 147-71
15) Dunbar S A et al. 2006; Clinica Chimica Acta (363) 71-82
16) Lee et al. 1997; Vox Sanguinis 73 (1): 1-11
17) Hashmi et al. 2005; Transfusion 45: 680-688
18) El Nemer W. et al. 1997; Blood 89 (12): 4608-4616
19) Irshaid et al. 1998; British Journal of Haematology 102: 1010-1014
20) Deregt D. et al. 2006; Journal of Virological Methods 136:7-23
21) Schmitt M. et al. 2006; J. Clin Microbiol (44) 2: 504-512
22) Diaz M. JCM August 2005; (43) 3662-3672

The invention claimed is:

1. A method for the identification and typing of at least one single nuclear polymorphism (SNP) of the erythrocyte system X for discriminating between heterozygote and homozygote individuals which comprises:

a) contacting said single nuclear polymorphism (SNP) with at least one set or more than one set of oligonucleotide probes amino-modified at the 5'-end, wherein said oligonucleotide probes have a sequence length ranging from 18 to 20 nucleotides containing at or near the center of the probe sequence, the specific single nuclear polymorphism (SNP) for each target alleles belonging to the erythrocyte system X that are selected from the group consisting of Kpa/Kpb, and Fya/Fyb, said probes being capable of specifically hybridizing to each of said target alleles; wherein said probes are coupled to a microsphere labeled with at least one fluorescent substance and consist of at least one probe/probe set of oligonucleotide sequences selected from the group consisting of Probe/probe set 1: Kpb/ATCACTTCACggCTgTTCCA (SEQ ID NO: 20) and Kpa ATCACTTCATggCTgTTC-CAg (SEQ ID NO:21); and probe/probe set 7: Fya/ GAgACTATggTgCCAACCTg (SEQ ID NO: 35) and Fyb TggAgACTATgATgCCAACC (SEQ ID NO: 36);

b) hybridizing said at least one set or more than one set of oligonucleotide probes to target alleles containing the one single nuclear polymorphism (SNP) at the following hybridization temperature ranges: probe set 1: 45-50° C.; and probe set 7: 52-56° C.; for the identification and typing of at least one single nuclear polymorphism (SNP) of an allelic pair X selected from the group consisting of Kpa/Kpb and Fya/Fyb using non-specific negative probes as control probes and c) detecting the presence of fluorescence with a flow cytometer-based instrument to identify and type said at least one single nuclear polymorphism (SNP) in order to discriminate between heterozygote and homozygote individuals wherein a negative control is used with probe set 1 consisting of AACTCTACggggCTCTTCgA (SEQ ID NO: 22); and a negative control is used with probe set 7 consisting of AggCTATCCTgACAAgCTT (SEQ ID NO: 37).

2. A method for the identification and typing of at least one single nucleotide polymorphism (SNP) of the erythrocyte system X in heterozygote and homozygote individuals for discriminating between homozygous and heterozygous samples, comprising the following phases:

a) extracting DNA from a biological sample;

b) amplifying by PCR, the genomic locus comprising the SNP of the erythrocyte system of interest, by means of at least one specific pair of primers for a target allele selected from the group consisting of: pair 1: Kpa/Kpb/ Fw: TgAggCCAggAgAAAAgCA (SEQ ID NO:3) and Rw: TgACCATCTggAAgAgCTTgC (SEQ ID NO:4); and pair 2:Fya/Fyb/Fw: CTTCCggTgTAACTCTgATgg (SEQ ID NO:13) and Rw:ATCCAgCAGGTTACAg-gAgT (SEQ ID NO:14) wherein at least one primer is biotinylated at the 5'-end with biotin to obtain biotinylated PCR products;

c) hybridizing the biotinylated PCR products obtained in step b) with one set or more than one set of oligonucleotide probes and adding streptavidin-phycoerythrin at a temperature for each probe/probe set at the following hybridization temperature ranges: probe set 1: 45-50° C.; and probe set 7: 52-56° C.;

Probe/probe set 1: Kpb ATCACTTCACggCTgTTCCA (SEQ ID NO: 20) and Kpa ATCACTTCATggCTgTTC-CAg (SEQ ID NO:21); and probe/probe set 7: Fya GAgACTATggTgCCAACCTg (SEQ ID NO: 35) and Fyb TggAgACTATgATgCCAACC (SEQ ID NO: 36);

d) detecting any fluorescence with a flow cytometer-based instrument to identify and type at least one single nucleotide polymorphism (SNP) of the erythrocyte system X in heterozygote and homozygote individuals in order to discriminate between heterozygote and homozygote individuals wherein a negative control used with probe set 1 consisting of is AACTCTACggggCTCTTCgA (SEQ ID NO: 22); and a negative control is used with probe set 7 consisting of AggCTATCCTgACAAgCTT (SEQ ID NO: 37).

3. The method of claim 2 wherein the target allele is Kpa/Kpb.

4. The method of claim 2 wherein the target alleles are Fya/Fyb.

5. The method of claim 1 wherein the target allele is Fya/Fyb.

* * * * *